US010912470B2

(12) United States Patent
Tong et al.

(10) Patent No.: US 10,912,470 B2
(45) Date of Patent: Feb. 9, 2021

(54) SYSTEM AND METHOD FOR TRACKING CEREBRAL BLOOD FLOW IN FMRI

(71) Applicants:Yunjie Tong, Belmont, MA (US); Blaise B. Frederick, Belmont, MA (US)

(72) Inventors: Yunjie Tong, Belmont, MA (US); Blaise B. Frederick, Belmont, MA (US)

(73) Assignee: MCLEAN HOSPITAL CORPORATION, Belmont, MA (US)

( * ) Notice: Subject to any disclaimer, the term of this patent is extended or adjusted under 35 U.S.C. 154(b) by 1285 days.

(21) Appl. No.: 15/034,792

(22) PCT Filed: Nov. 7, 2014

(86) PCT No.: PCT/US2014/064601
§ 371 (c)(1),
(2) Date: May 5, 2016

(87) PCT Pub. No.: WO2015/070046
PCT Pub. Date: May 14, 2015

(65) Prior Publication Data
US 2016/0287100 A1 Oct. 6, 2016

Related U.S. Application Data

(60) Provisional application No. 61/901,795, filed on Nov. 8, 2013.

(51) Int. Cl.
*A61B 5/026* (2006.01)
*G01R 33/48* (2006.01)
(Continued)

(52) U.S. Cl.
CPC .......... *A61B 5/0263* (2013.01); *A61B 5/0042* (2013.01); *A61B 5/0295* (2013.01);
(Continued)

(58) Field of Classification Search
CPC ..... A61B 5/0263; A61B 5/055; A61B 5/0042; A61B 5/7207; A61B 5/7246;
(Continued)

(56) References Cited

U.S. PATENT DOCUMENTS

| 8,339,138 B2 | 12/2012 | Parker et al. |
| 2013/0144140 A1 | 6/2013 | Frederick et al. |
| 2013/0144154 A1* | 6/2013 | Villringer .......... G01R 33/4806 600/410 |

FOREIGN PATENT DOCUMENTS

| WO | 2004109300 | 12/2004 |
| WO | WO-2011153521 A2 * | 12/2011 ........... A61B 5/4312 |
| WO | 2012/040219 | 3/2012 |

OTHER PUBLICATIONS

Le et al., "Identifying the Perfusion Deficit in Acute Stroke with Resting-State Functional Magnetic Resonance Imaging", Aug. 31, 2012, Annals of Neurology, vol. 73, No. 1, pp. 136-139 (Year: 2012).*

(Continued)

*Primary Examiner* — Boniface N Nganga
(74) *Attorney, Agent, or Firm* — Quarles & Brady LLP

(57) ABSTRACT

A system and method for analyzing blood flow in a subject's brain is provided. In some aspects, the method includes analyzing fMRI data to identify signals related to blood flow, and selecting a zero time lag seed regressor using the identified signals. The method also includes correlating the selected seed regressor to identify a subset of the fMRI data that correlates with the seed regressor and is offset in time, combining the subset of the data to determine a time-delayed regressor, and performing repetitions to obtain a number of time-delayed regressors, where for each repetition, the seed regressor is adjusted using a previous time-delayed regressor. The method further includes analyzing the data using the time-delayed regressors to determine blood delivery from (Continued)

vessels across the brain, and generating a report. In some aspects, a second recursive procedure may be performed using an optimized seed regressor obtained from a first recursive procedure.

13 Claims, 16 Drawing Sheets

(51) Int. Cl.
    A61B 5/055     (2006.01)
    G01R 33/563    (2006.01)
    G01R 33/565    (2006.01)
    A61B 5/00      (2006.01)
    A61B 5/0295    (2006.01)
(52) U.S. Cl.
    CPC ............ *A61B 5/055* (2013.01); *A61B 5/7207* (2013.01); *A61B 5/7246* (2013.01); *G01R 33/4806* (2013.01); *G01R 33/56366* (2013.01); *G01R 33/56509* (2013.01); *G01R 33/56545* (2013.01); *A61B 2576/026* (2013.01)
(58) Field of Classification Search
    CPC ........ G01R 33/56509; G01R 33/56545; G01R 33/4806; G01R 33/56366; A81B 2567/026
    See application file for complete search history.

(56) References Cited

OTHER PUBLICATIONS

Aalkjaer C, et al (2011): Vasomotion—What is currently thought? Acta Physiol (Oxf) 202:253-269.
Aguirre, G.K., et al., 2005. Perfusion fMRI for functional neuroimaging. International review of neurobiology 66, 213-236.
Allen J, et al (2003): Age-related changes in the characteristics of the photoplethysmographic pulse shape at various body sites. Physiol Meas 24:297-307.
Bandettini PA, et al (1992): Time course EPI of human brain function during task activation. Magn Reson Med 25:390-397.
Behzadi Y, et al (2007): A component based noise correction method (CompCor) for BOLD and perfusion based fMRI. NeuroImage 37:90-101.
Bhattacharyya PK, et al (2004): Cardiac-induced physiologic noise in tissue is a direct observation of cardiac-induced fluctuations. Magn Reson Imaging 22:9-13.
Birn RM, et al (2008): The respiration response function: The temporal dynamics of fMRI signal fluctuations related to changes in respiration. NeuroImage 40: 644-654.
Buchel, C. et al. "Dynamic changes in effective connectivity characterized by variable parameter regression and Kalman filtering." Human brain mapping 65-6 (1998): 403-408.
Carbonell F, et al (2011): Global and system-specific resting-state fMRI fluctuations are uncorrelated: principal component analysis reveals anti-correlated networks. Brain Connect 1:496-510.
Chang C, et al (2009): Influence of heart rate on the BOLD signal: The cardiac response function. NeuroImage 44:857-869.
Chen, Y., et al. (2011). "Test-retest reliability of arterial spin labeling with common labeling strategies." Journal of magnetic resonance imaging : JMRI 33(4): 940-949.
Churchill NW, et al (2013): PHYCAA1: An optimized, adaptive procedure for measuring and controlling physiological noise in BOLD fMRI. NeuroImage 82:306-325.
Cordes D, et al (2001): Frequencies contributing to functional connectivity in the cerebral cortex in "resting-state" data. AJNR Am J Neuroradiol 22:1326-1333.
Crandell, D., et al. (1973). "Cerebral transit time of 99m technetium sodium pertechnetate before and after cerebral arteriography." Journal of neurosurgery 38(5): 545-547.

D'Esposito M, et al (2003): Alterations in the BOLD fMRI signal with ageing and disease: a challenge for neuroimaging. Nat Rev Neurosci, 4:863-872.
Essig, M., et al. (2013). "Perfusion MRI: the five most frequently asked technical questions." AJR. American journal of roentgenology 200(1): 24-34.
Feinberg, D. A., et al. (2010). "Multiplexed echo planar imaging for sub-second whole brain FMRI and fast diffusion imaging." PloS one 5(12): e15710.
Frederick B, et al (2012): Physiological denoising of BOLD fMRI data using Regressor Interpolation at Progressive Time Delays (RIPTiDe) processing of concurrent fMRI and near-infrared spectroscopy (NIRS) NeuroImage 60:1913-1923.
Herman P, et al (2001): Fractal branching pattern in the pial vasculature in the cat. J Cereb Blood Flow Metab 21: 741-753.
Ibaraki M, et al (2007): Cerebral vascular mean transit time in healthy humans: A comparative study with PET and dynamic susceptibility contrast-enhanced MRI. J Cereb Blood Flow Metab 27:404-413.
Jenkinson M, et al (2002): Improved optimization for the robust and accurate linear registration and motion correction of brain images. NeuroImage 17:825-841.
Jenkinson M, et al (2012): Fsl. NeuroImage 62:782-790.
Julien C (2006): The enigma of Mayer waves: Facts and models. Cardiovasc Res 70:12-21.
Kim, S.G., 2012. Perfusion MR imaging: evolution from initial development to functional studies. NeuroImage 62, 672-675.
Knutsson L, et al (2010): Absolute quantification of perfusion using dynamic susceptibility contrast MRI: Pitfalls and possibilities. MAGMA 23:1-21.
Koretsky, A.P., 2012. Early development of arterial spin labeling to measure regional brain blood flow by MRI. NeuroImage 62,602-607.
Leopold DA, et al (2012): Ongoing physiological processes in the cerebral cortex. NeuroImage 62:2190-2200.
McGehee, B.E., et al., 2012. Brain perfusion imaging: How does it work and what should I use? Journal of magnetic resonance imaging : JMRI 36,1257-1272.
Menon RS (2012): The great brain versus vein debate. NeuroImage 62:970-974.
Murphy K, et al (2011): Robustly measuring vascular reactivity differences with breath-hold: Normalising stimulus-evoked and resting state BOLD fMRI data NeuroImage 54:369-379.
Murphy K, et al (2013): Resting-state fMRI confounds and cleanup. NeuroImage 80:349-359.
Ogawa S, et al (1992): Intrinsic signal changes accompanying sensory stimulation: Functional brain mapping with magnetic resonance imaging. Proc Natl Acad Sci USA 89:5951-5955.
Perlbarg V, et al (2007): CORSICA: Correction of structured noise in fMRI by automatic identification of ICA components. Magn Reson Imaging 25:35-46.
Reishofer G, et al (2012): Fractal dimension and vessel complexity in patients with cerebral arteriovenous malformations. PLoS One 7:e41148.
Sassaroli, A., et al., 2012. Low-Frequency Spontaneous Oscillations of Cerebral Hemodynamics Investigated With Near-Infrared Spectroscopy: A Review. IEEE Journal of Selected Topics in Quantum Electronics PP.
Scholvinck ML, et al (2010): Neural basis of global resting-state fMRI activity. Proc Natl Acad Sci USA 107:10238-10243.
Schreiber SJ, et al (2002): Dopplersonographic measurement of global cerebral circulation time using echo contrast-enhanced ultrasound in normal individuals and patients with arteriovenous malformations. Ultrasound Med Biol 28:453-458.
Shmueli K, et al (2007): Low-frequency fluctuations in the cardiac rate as a source of variance in the resting-state fMRI BOLD signal. NeuroImage 38:306-320.
Smith, S. M., et al. (2004). "Advances in functional and structural MR image analysis and implementation as FSL." NeuroImage 23 Suppl 1: S208-219.
Tanaka Y, et al (2006): Quantitative evaluation of cerebral hemodynamics in patients with moyamoya disease by dynamic susceptibility

(56) References Cited

OTHER PUBLICATIONS contrast magnetic resonance imaging—Comparison with positron emission tomography. J Cereb Blood Flow Metab 26:291-300.

Tong Y, et al (2010): Time lag dependent multimodal processing of concurrent fMRI and near-infrared spectroscopy (NIRS) data suggests a global circulatory origin for low-frequency oscillation signals in human brain. NeuroImage 53: 553-564.

Tong Y, et al (2011): Partitioning of physiological noise signals in the brain with concurrent near-infrared spectroscopy and fMRI. J Cereb Blood Flow Metab 31:2352-2362.

Tong Y, et al (2012): Low-frequency oscillations measured in the periphery with near-infrared spectroscopy are strongly correlated with blood oxygen leveldependent functional magnetic resonance imaging signals. J Biomed Opt 17:106004.

Tong Y, et al (2013): Evaluating the effects of systemic low frequency oscillations measured in the periphery on the independent component analysis results of resting state networks. NeuroImage 76:202-215.

Tong, Y., et al., 2012. Concurrent fNIRS and fMRI processing allows independent visualization of the propagation of pressure waves and bulk blood flow in the cerebral vasculature. NeuroImage 61, 1419-1427.

Wise RG, et al (2004): Resting fluctuations in arterial carbon dioxide induce significant low frequency variations in BOLD signal. NeuroImage 21:1652-1664.

Zhu, S., et al., 2013. Resting state brain function analysis using concurrent BOLD in ASL perfusion fMRI. PloS one 8, e65884.

Zou QH, et al (2008): An improved approach to detection of amplitude of low-frequency fluctuation (ALFF) for resting-state fMRI: Fractional ALFF. J Neurosci Methods 172:137-141.

Zuo XN, et al (2010): The oscillating brain: Complex and reliable. NeuroImage 49:1432-1445.

International Search Report and Written Opinion dated Apr. 7, 2015 for International Application No. PCT/US2014/064601.

Sadaghiani, S., et al., "Intrinsic Connectivity Networks, Alpha Oscillations, and Tonic Alertness: a Simultaneous Electroencephalography/Functional Magnetic Resonance Imaging Study," in The Journal of Neuroscience, Jul. 28, 2010, vol. 30, pp. 10244-10246.

Tong, Y. et al., "An improved method of mapping cerebrovascular reserve using concurrent fMRI and near infrared spectroscopy with Regressor Interpolation at Progressive Time Delays(RIPTiDe)" in Neuroimage, Jun. 15, 2011, vol. 56, p. 6.

Tong, Y, et al., "Tracking cerebral blood flow in BOLD fMRI using recursively generated regressors" in Human Brain Mapping, Published online Jun. 23, 2014 in Wiley Online Library (wileyonlinelibrary.com), pp. 5471-5485.

\* cited by examiner

SYSTEM AND METHOD FOR TRACKING CEREBRAL BLOOD FLOW IN FMRI

CROSS-REFERENCE TO RELATED APPLICATIONS

This application represents the U.S. National Stage of International Application No. PCT/US2014/064601, filed Nov. 7, 2014 which is based on, claims priority to, and incorporates herein by reference in their entirety, U.S. Provisional Application Ser. No. 61/901,795, filed Nov. 8, 2013, and entitled, "SYSTEM AND METHOD FOR TRACKING CEREBRAL BLOOD FLOW IN fMRI."

STATEMENT REGARDING FEDERALLY SPONSORED RESEARCH

This disclosure was made with government support under DA031769 and DA32746 awarded by the National Institutes of Heath. The government has certain rights in the disclosure.

BACKGROUND OF THE DISCLOSURE

The present disclosure generally relates to systems and methods for functional magnetic resonance imaging (fMRI) techniques, and in particular, the use of fMRI to track blood flow in a subject.

Perfusion is an important physiological and patho-physiological parameter that reflects the basic and vital function of blood delivery to different parts of the body. In the brain, even minor alterations to brain perfusion can significantly impact neuronal activity and hence physiological functionality. To identify processes associated with brain perfusion, many magnetic resonance imaging (MRI) methods have been developed that can assess multiple perfusion parameters, such as blood flow, blood volume, mean transit time, time to peak, and so on. In general, such perfusion methods utilize intravascular tracer mechanisms, or contrast mechanisms, whose signature signals can be detected spatially and temporally while imaging specific regions of interest (ROIs).

Contrast mechanisms utilized in MRI can be exogenous or endogenous contrasts. Specifically, exogenous contrasts require administration of a contrast agent, normally a chelated gadolinium compound, that is injected intravenously in a bolus during a perfusion imaging procedure. However, exogenous contrast agents can present a potential toxicity to some patients, requiring careful screening and monitoring before and during the procedure. In addition, many exogenous contrast agents are incapable of crossing the blood-brain barrier (BBB), hence limiting applicability with respect to perfusion studies on the brain.

Endogenous contrast mechanisms, on the other hand, are generated by magnetically labeling native protons in blood water using special MRI sequences, such as arterial spin labeling (ASL) sequences. Specifically, protons are labeled at specific location in the body, typically the carotid arteries, and changes in the MR signal are then monitored as the labeled water arrives at remote locations. Although endogenous contrast mechanisms are non-noninvasive, they can have substantially lower signal to noise, and lower temporal resolution. In addition, use of endogenous contrasts presents a lack of sensitivity to tag delays outside a predetermined range, which is frequently the case in abnormal blood circulation. Despite some recent developments, the low temporal resolution remains especially problematic for functional studies.

Considering the above drawbacks, there continues to be a clear need for non-invasive systems and methods directed to identifying regional blood flow, such as cerebral blood flow, and tracking blood flow changes in an imaged subject.

SUMMARY OF THE DISCLOSURE

The present disclosure overcomes the aforementioned drawbacks by providing a system and method for tracking global cerebral blood flow and regional blood flow changes in an imaged subject using functional MRI data. Specifically, a novel data-driven approach is provided, whereby temporal traces of systemic oscillations in blood oxygen level dependent (BOLD) signals may be effectively extracted via a recursive process, and used to derive blood circulation maps.

In one aspect of the present disclosure, a method is provided for analyzing blood flow in the brain of a subject. The method includes acquiring a set of functional magnetic resonance imaging (fMRI) data from the subject over a time period with a magnetic resonance imaging (MRI) system. The method also includes analyzing the set of fMRI data to identify a target spectral characteristic related to blood flow in at least one vessel coupled to the brain and selecting, from the set of fMRI data, a seed regressor as a zero time lag signal with the target spectral characteristic. The method further includes performing a cross-correlation using the set of fMRI data and the seed regressor to identify a subset of the set of fMRI data that correlates with the seed regressor greater than a threshold and is offset from the zero time lag signal. The method then includes combining the subset of the set of fMRI data to determine a time-delayed regressor and repeating the preceding steps to obtain a number of time-delayed regressors. For each corresponding repetition, the seed regressor is adjusted using the time-delayed regressor. The method also includes analyzing the set of fMRI data using the plurality of time-delayed regressors to determine a delivery of blood from the at least one vessel across regions of the brain and generating a report of regional blood flow changes in the brain of the subject over the time period.

In another aspect of the present disclosure, a magnetic resonance imaging (MRI) system is disclosed that is configured for analyzing blood flow in the brain of a subject. The system includes a magnet system configured to generated a polarizing magnetic field about at least a portion of the subject arranged in the MRI system and a plurality of gradient coils configured to apply a gradient field to the polarizing magnetic field. The system also includes a radio frequency (RF) system configured to apply an excitation field to the subject and acquire, over a time period, functional magnetic resonance imaging (fMRI) data that measures at least one of a blood flow, a blood volume, and a blood oxygenation of the subject. The system further includes a computer system programmed to control operation of the plurality of gradient coils and RF system to acquire a set of fMRI data and analyze the set of fMRI data to identify a target spectral characteristic related to blood flow in at least one vessel coupled to the brain. The computer is further caused to select, from the set of fMRI data, a seed regressor associated with a zero time lag signal, and consistent with the target spectral characteristic and perform a cross-correlation using the set of fMRI data and the seed regressor to identify a subset of the set of fMRI data that correlates with the seed regressor greater than a threshold and is offset from the zero time lag signal. The computer is also caused to combine the subset of the set of fMRI data to determine a time-delayed regressor and repeat the preceding steps to obtain a number of time-delayed regressors, wherein for each corresponding repetition, the seed regressor is adjusted using the time-delayed regressor. The computer is further configured to analyze the set of fMRI data using the plurality of time-delayed regressors to determine a delivery of blood from the at least one vessel across regions of the brain and generate a report of regional blood flow changes in the brain of the subject over the time period.

In yet another aspect of the present disclosure, a method for analyzing blood flow in the brain of a subject is provided. The method includes receiving a set of time-series functional data acquired from a subject, and selecting, from the set of time-series functional data, a seed regressor having a target characteristic. The method also includes performing a cross-correlation using the set of time-series functional data and the seed regressor to identify time-series correlates that are offset in time, and combining the time-series correlates to determine a time-delayed regressor. The method further includes performing a repetition to obtain a number of time-delayed regressors, wherein for each corresponding repetition, the seed regressor is adjusted using a corresponding time-delayed regressor, and utilizing each of the generated regressors in a statistical analysis of the functional data to determine blood flow changes in the brain of the subject over time.

The foregoing and other aspects and advantages of the disclosure will appear from the following description. In the description, reference is made to the accompanying drawings which form a part hereof, and in which there is shown by way of illustration a preferred embodiment of the disclosure. Such embodiment does not necessarily represent the full scope of the disclosure, however, and reference is made therefore to the claims and herein for interpreting the scope of the disclosure.

BRIEF DESCRIPTION OF THE DRAWINGS

The present disclosure will hereafter be described with reference to the accompanying drawings, wherein like reference numerals denote like elements.

DETAILED DESCRIPTION OF THE DISCLOSURE

Functional MRI (fMRI) has been widely used in analyses of brain function. In particular, recent approaches have utilized Blood Oxygen Level Dependent (BOLD) signals to demonstrate local and systemic changes in blood flow, volume and oxygenation. In general, BOLD data is dominated by low frequency oscillations (LFOs), roughly in a frequency range between 0.01 and 0.1 Hertz, whose origins remain unclear, and commonly treated as physiological noise in standard fMRI studies.

In previous studies by the inventors, it was shown that low frequency oscillations found in BOLD fMRI are systemic signals closely related to the blood circulation. Application of specialized data analysis methods revealed temporal shifts between BOLD signals associated with different voxels, indicating relative arrival times between voxels of the blood borne LFO signal. Similarly, LFO signals were also detected from near infrared spectroscopy (NIRS) signals measuring changes in total hemoglobin concentration at peripheral parts of the body (e.g. fingertips or toes). Based on these features of the LFOs, dynamic cerebral blood circulation was determined by using temporally shifted NIRS signals and simultaneously with fMRI data as regressors to derive a map of the propagation of the LFOs in the brain.

However, there are limitations to the above technique. First, NIRS instruments are not widely available. Second, the NIRS signal reflects blood fluctuation either in a superficial layer of the tissue (i.e., from forehead measurement) or in the periphery. As the blood flowing to these areas diverges from that which flows towards the brain, the shape of the signal might not accurately predict the shape of cerebral LFOs, despite the temporal shifts. Given the systematic changes in blood flow in the extremities that occur as a result of aging, and the spatially heterogeneous age-dependent changes in cerebral vascular tone and flow resistance, this limitation may be exacerbated in older patients. Third, and importantly, the time-shifted regressors from NIRS are static. However, LFO time courses may vary as the blood propagates through the brain, due to the complicated and inhomogeneous cerebral vasculature structure (i.e., arteries, veins, and capillaries).

By contrast, the present disclosure describes a data-driven approach that may be performed independently from functional analyses, allowing assessment of information about cerebral blood flow to be conducted in parallel with function studies. As will be described, regressors are derived using acquired BOLD signals via a recursive process, and utilized in a general linear model analysis to track cerebral blood circulation. In some aspects of the present disclosure, a second, optimized recursive procedure may be utilized to improve the accuracy of the tracked cerebral blood circulation, taking into account regional fluctuations and noise.

Figure 1:
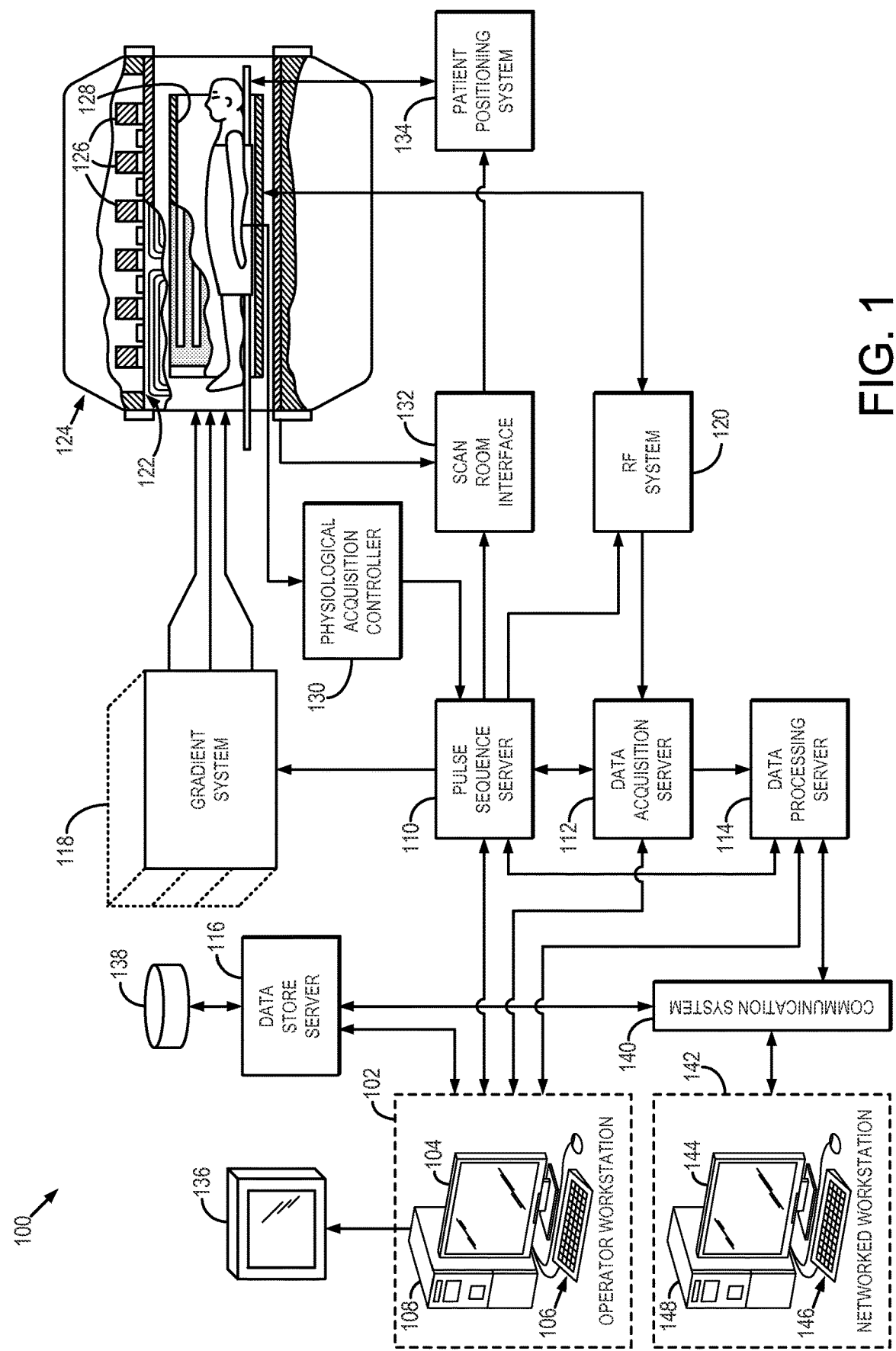
FIG. 1 is a schematic block diagram of an exemplary MR imaging system for use in accordance with the present disclosure.

Referring particularly to FIG. 1, an example of a magnetic resonance imaging ("MRI") system 100 is illustrated. The MRI system 100 includes an operator workstation 102, which will typically include a display 104; one or more input devices 106, such as a keyboard and mouse; and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \tag{1};$$

and the phase of the received magnetic resonance signal may also be determined according to the following relationship:

$$\varphi = \tan^{-1}\left(\frac{Q}{I}\right). \tag{2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during pre-scans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data;

performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

Figure 2:
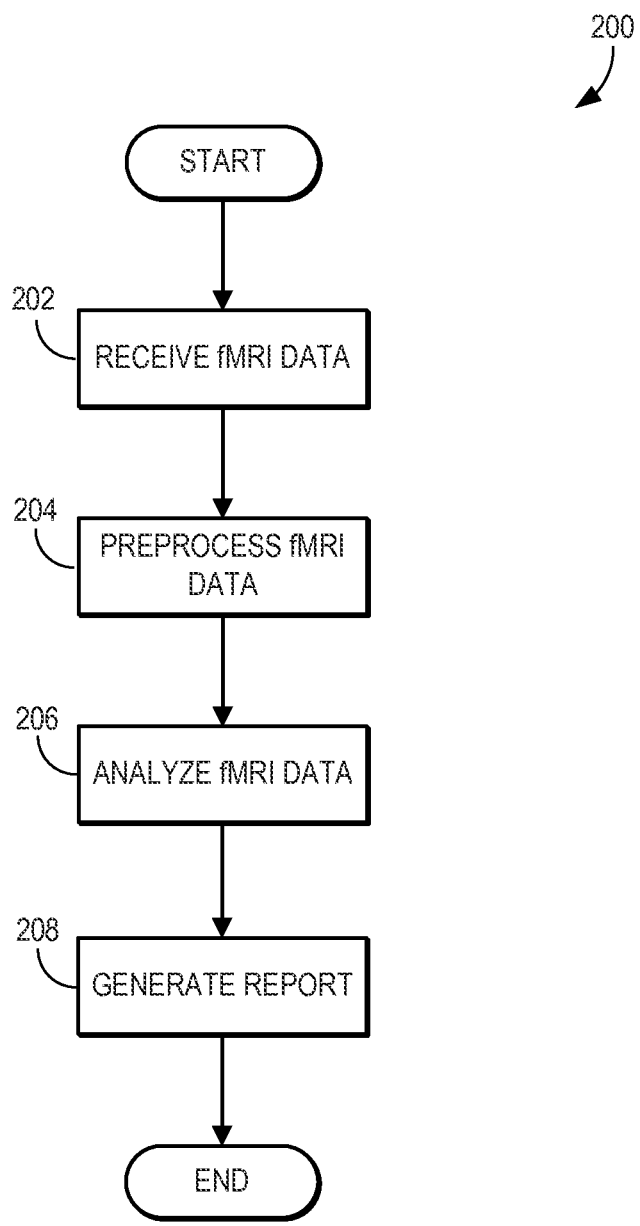
FIG. 2 is a flow diagram depicting an example of steps associated with providing blood flow indicators using a data-driven method, in accordance with the present disclosure.

Turning now to FIG. 2, an example process 200 of operation according to the present disclosure is illustrated. The process 200 begins at process block 202 where time-dependent functional MRI (fMRI) data, such as BOLD fMRI data, along with any other desirable data, for example, anatomical MRI data, may be received. In some aspects, such data may be received, for example, through a data acquisition process performed using, for example, a system similar to the above-described MRI system. In other aspects, fMRI and other data may be accessed from a memory, database, or other storage medium.

At process block 204 the MRI data may be pre-processed using a number of pre-processing steps. In particular, the fMRI data may undergo a combination of pre-processing steps, including motion correction, slice timing correction, and spatial smoothing (e.g. 5 mm). Alternatively, the pre-processing at block 204 may be omitted, for example, if the accessed data were previously processed or the clinical application does not benefit from pre-processing. Then, at process block 206 the fMRI data may be analyzed, using any system suitable. For example, a statistical analysis process, in accordance with aspects of the present disclosure, may be performed on any personal computer, laptop, tablet, workstation, or any other computing device configured to do so.

After completion of the analysis performed at process block 206 as will be described below, at process block 208, a report is generated. The report may take any shape or form, as desired or required. In one aspect, the report may include any combination of dynamic z-statistic maps, correlation maps, or time delay maps, and so forth, providing indication of blood circulation or brain activation.

Figure 3:
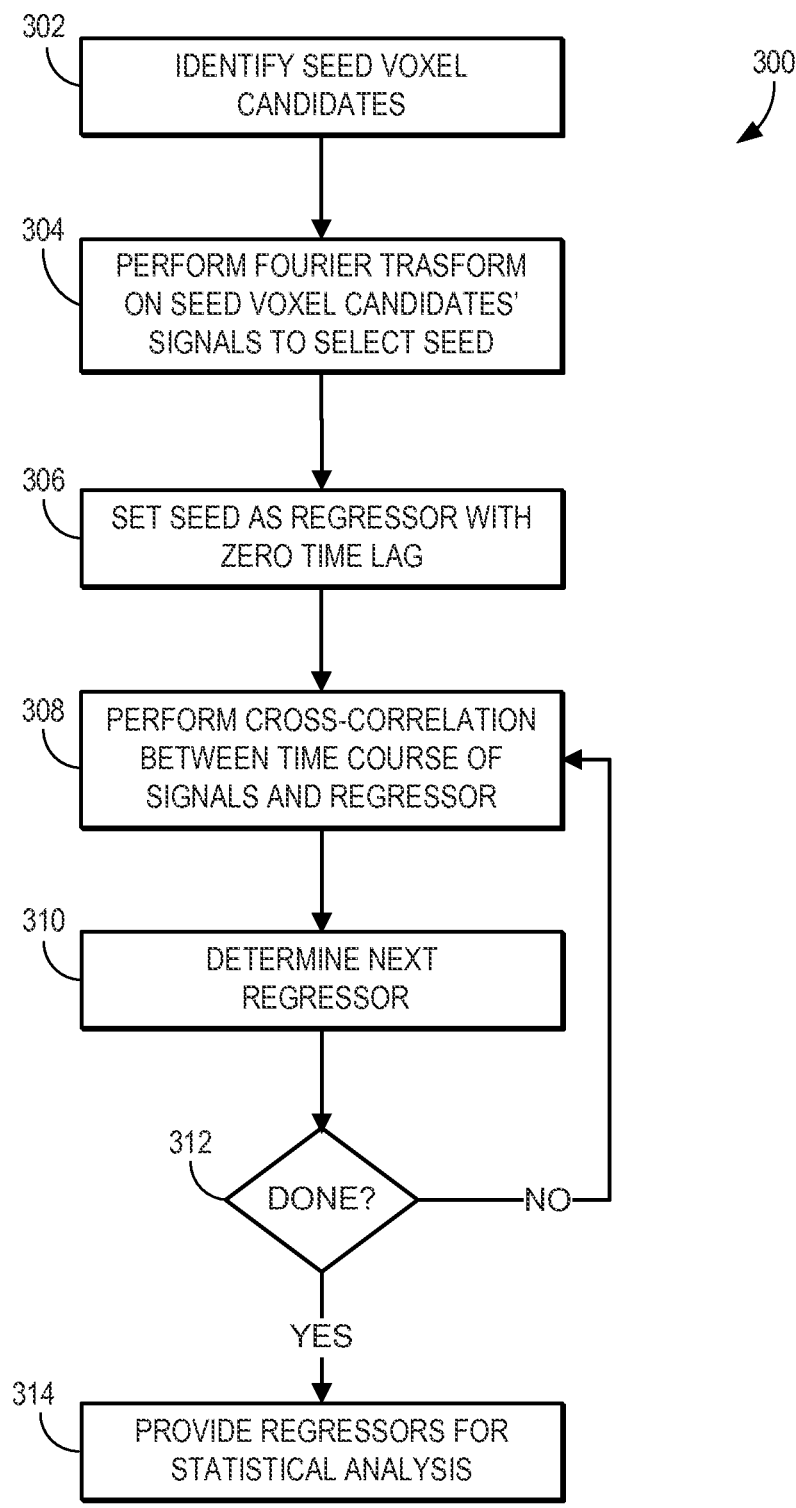
FIG. 3 is a flow diagram depicting an example of steps associated with analysis of fMRI data, in accordance with the present disclosure.

One example of an analysis process such as may be performed at process block 206 is illustrated by a process 300 provided in FIG. 3. The process 300 begins at process block 302 wherein a number of seed voxel candidates having information about blood flow are identified using a set of pre-determined criteria applied to regions of interest (ROI) in the images generated from received time-series fMRI data, as described below. In some aspects of the present disclosure, and in contrast to typical BOLD fMRI analyses, BOLD signal changes caused by neuronal activation may be regarded as "noise."

Figure 4A:
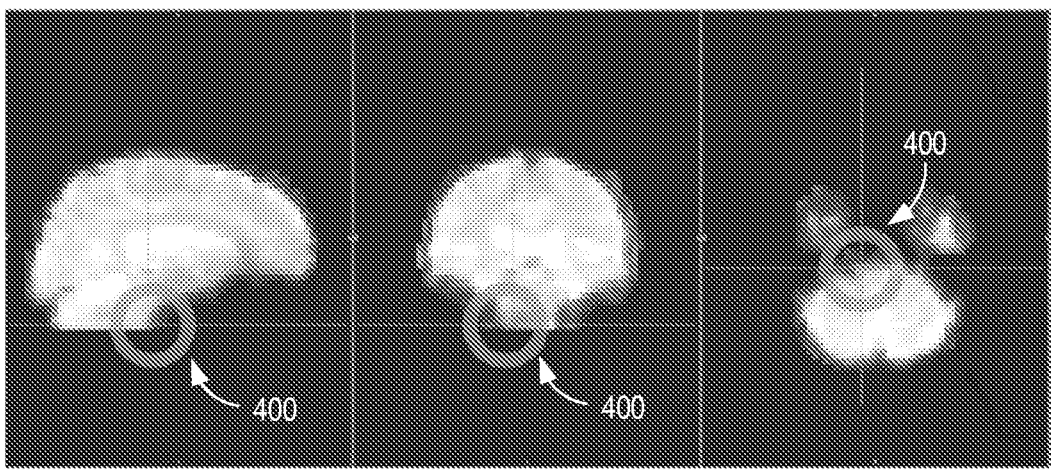
FIG. 4A shows an example of orthogonal functional MRI (fMRI) images of a subject, illustrating a seed location in the bottom slice of an fMRI data set, in accordance with the present disclosure.
Figure 4B:
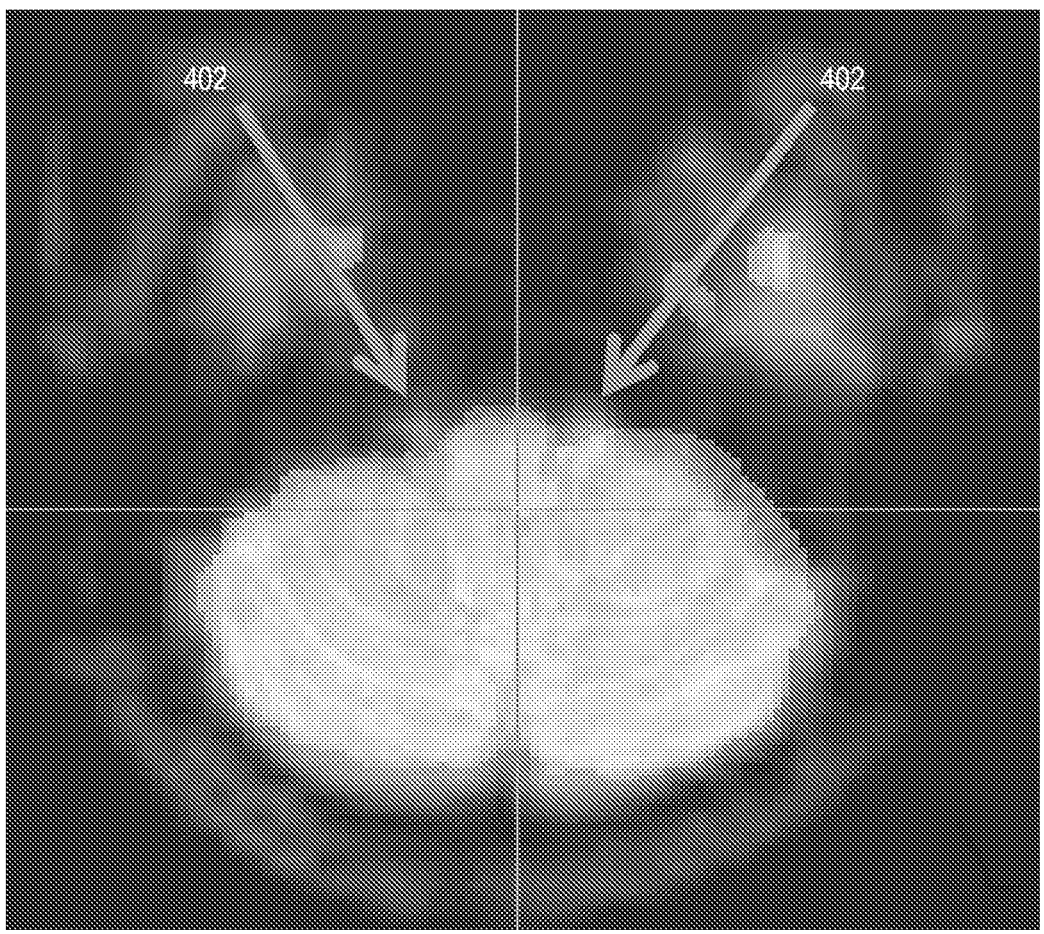
FIG. 4B shows an example of a bottom slice of an fMRI image set projected onto a structural image, where the arrows indicate the veins on each side of the Pons.

Specifically, candidate seed voxel identification may be performed manually as directed by a user, or autonomously or semi-autonomously, such as by performing automatic segmentation based on predetermined criteria for identifying regions of interest (ROIs) or particular areas identifiable as including information about blood flow. For example, it may be advantageous to select seed regions that avoid robust neuronally-derived BOLD signal changes. Identifying regions containing minimal brain tissue (e.g. gray matter) but a great amount of blood vessels, represents one preferred way of enhancing desired signals while avoiding such undesired noise. Such desirable regions may, for example, be located in the bottom slice of a typical axial fMRI scan, where vessels are relatively large and easy to identify. Suitable blood vessel voxels, such as those form arteries or veins, may be identified by search in an area surrounding the Pons, which can be easily identified on the bottom slice, as it is surrounded by large blood vessels. Examples of vessels include Clival venous plexus, Petrosal vein, Jugular bulb, Basilar artery, and so forth. By way of example, FIG. 4A shows three orthogonal fMRI images of a subject, illustrating potential seed locations 400 on the bottom slice of the fMRI images. Specifically, in the sagittal slice, a voxel may be chosen at the boundary of the cortex. FIG. 4B shows the bottom slice of the fMRI image set projected onto a structural image, where the arrows indicate large veins 402 on each side of the Pons.

Figure 4C:
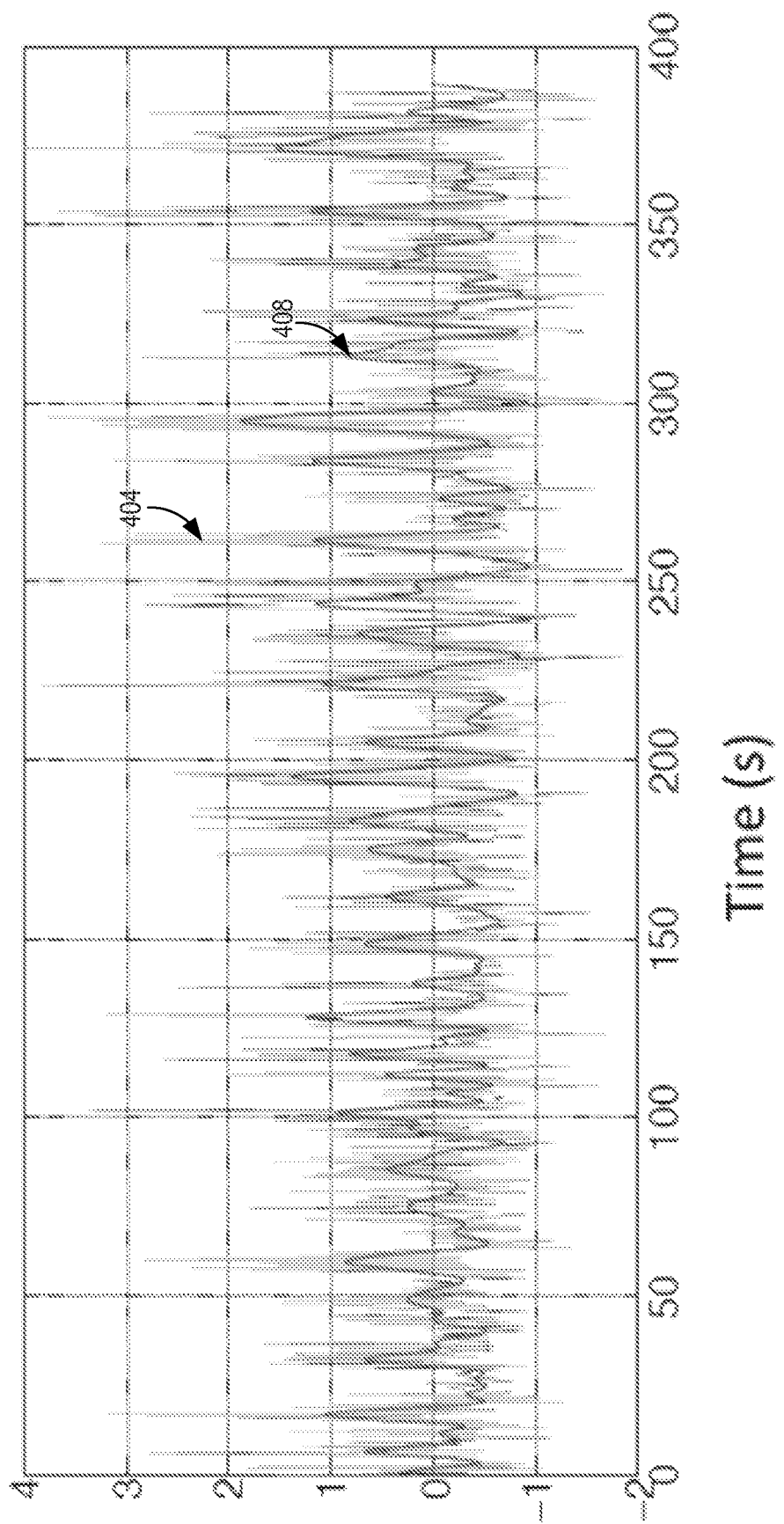
FIG. 4C is a graphical depiction illustrating an example temporal trace of a fMRI BOLD signal, in accordance with the present disclosure.
Figure 4D:
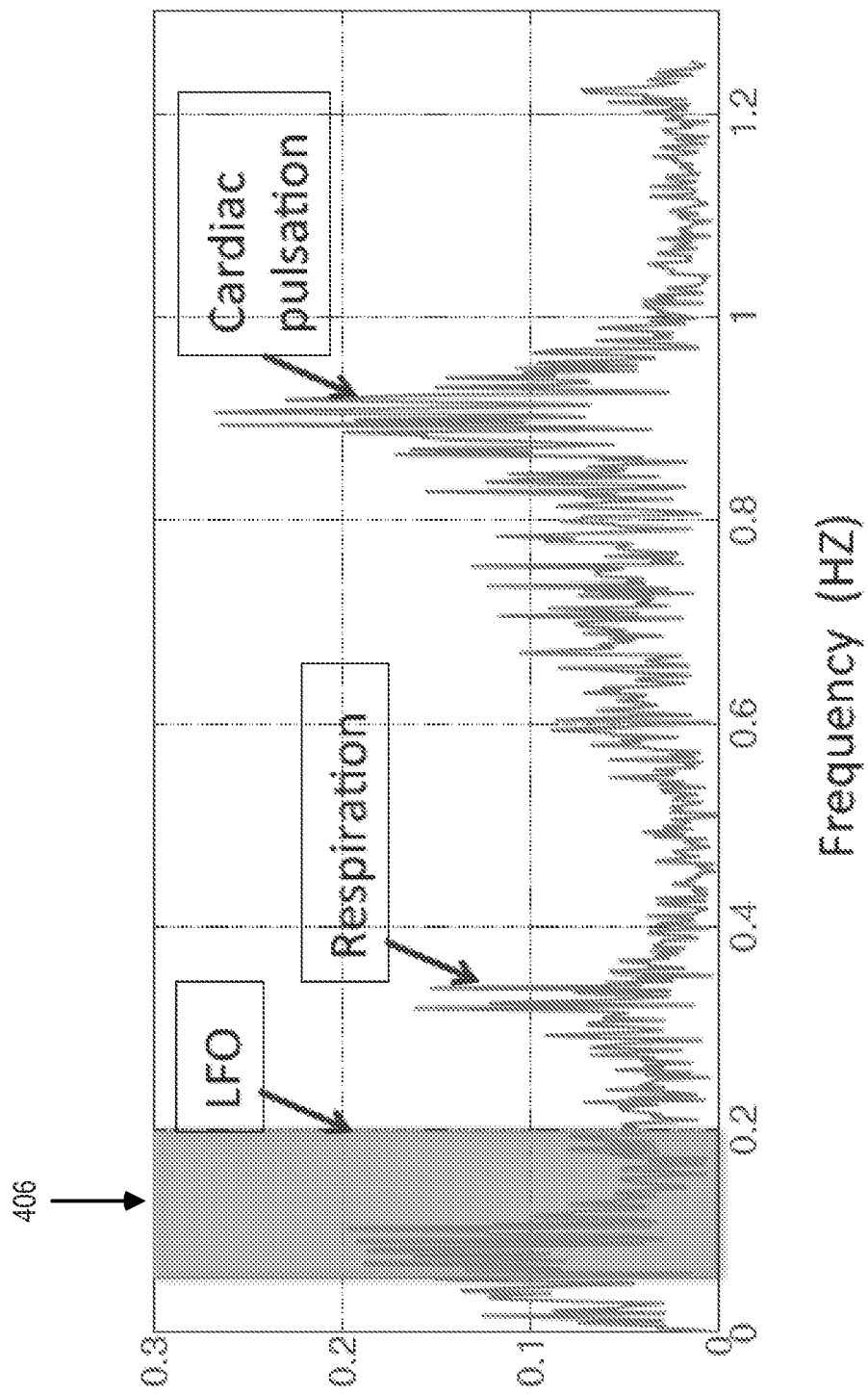
FIG. 4D is a graphical depiction illustrating an example of a power spectrum for a temporal trace of a fMRI BOLD signal, in accordance with the present disclosure.

Referring again to FIG. 3, in selecting a seed with target characteristics, at process block 304, a Fourier transform may be performed on the BOLD signals associated with each of the candidate seed voxels identified at process block 302. Voxels with distinct components in the low frequency domain (for example, less than 0.2 Hz), together with physiological components representing cardiac pulsation, are likely to be suitable seeds. FIG. 4C shows an example of the temporal trace 404 of a candidate seed voxel, selected as described above. The corresponding frequency spectrum is given in FIG. 4D, whereby distinct peaks in the low frequency domain, indicative of LFO, as well as respiration and cardiac frequencies are shown.

In some aspects, the pre-processed fMRI data may be filtered to enhance signals in a desired frequency range. For example, by applying a zero delay bandpass filter in the frequency range between, say, 0.05 and 0.2 Hz, systemic LFO may be retained in the acquired BOLD signals. A low frequency range 406 of a bandpass filter is highlighted in the example power spectrum of FIG. 4D. The resulting time trace 408 resulting from a filtering step, as indicated, is shown in FIG. 4C. As appreciated from FIG. 4C, application of the filter in the frequency range of the LFO is shown to result in a smoother temporal trace as compared to the raw, unfiltered data shown by temporal trace 404.

Referring again to FIG. 3, once a seed voxel has been selected at process block 304, the extracted time course for the selected seed voxel may then be set as a seed regressor with zero time lag at process block 306. Then at process block 308 a voxel-wise cross-correlation is calculated between the time courses of the BOLD signals and the zero time lag seed regressor.

Determination of the next regressor then begins at process block 310 by identifying voxels whose respective BOLD time-series signals satisfy a pre-defined selection criterion. Specifically, a selection criterion may include voxels whose maximum cross correlation between the BOLD time-series signal and seed regressor time-series are higher than a threshold value, such as 0.5. In addition, voxels whose time lag of the maximum cross correlation occurs at a specified temporal value may also be selected. By way of example, the repetition time (TR) of an imaging acquisition sequence can be used to determine the temporal resolution of the time lag. Specifically, a selected time lag of "+1" (or "−1") means a time shift is +1 (or −1) times TR between the seed regressor and the signals of the candidate voxel. In particular, a selected negative lag value of −1 TR, corresponds to voxels where blood arrives prior to arrival at the current seed voxel. For instance, a repetition time may be in the range between 100 milliseconds and 3000 milliseconds, although other values may be possible.

The above selection criterion ensures that only highly-correlated voxels (for example, those greater than 0.5), and those within a specified time frame (for example, with a time lag +1 or −1 TR) with respect to the seed regressor are selected. In addition, defining the sign of the lag value allows search of voxels in either upstream (prior to arrival at the current seed) or downstream (after arrival at the current seed).

Then, at the end of process block 310, BOLD time-series signals, or time-series correlates that are offset in time, that satisfy the selection criterion above can be combined together to generate a new regressor time-series for the next iteration step. Specifically, the identified BOLD time-series signals may be averaged together, and the result may be set as the next upstream or downstream regressor.

After evaluating an exit condition at process block 312, an indication of continued iteration may dictate a return to process block 308, where the regressor determined at process block 310 may then be used in a repeated cross-correlation calculation that begins again with process block 308. As such, process blocks 308 through 312 may be repeated for a number of iterations to generate multiple self-evolving regressors, until the exit condition at process block 312 is satisfied. Iteration exit condition at process block 312 may be satisfied when the number of voxels found at process block 308 is less than a predetermined threshold value. For example, the predetermined threshold value may be 100, although other values are possible. In this manner, a number of regressors may be generated with time lags ±1TR, ±2 TR, ±3TR, and so forth, with respect to the seed regressor. Subsequently, at process block 314, regressors obtained from repeated iterations, as described above, are provided to perform a statistical analysis indicative of cerebral blood flow or neuronal activation property. As mentioned, such analysis may result in computed dynamic z-statistic maps, correlation maps, time delay maps, and so forth.

Figure 5:
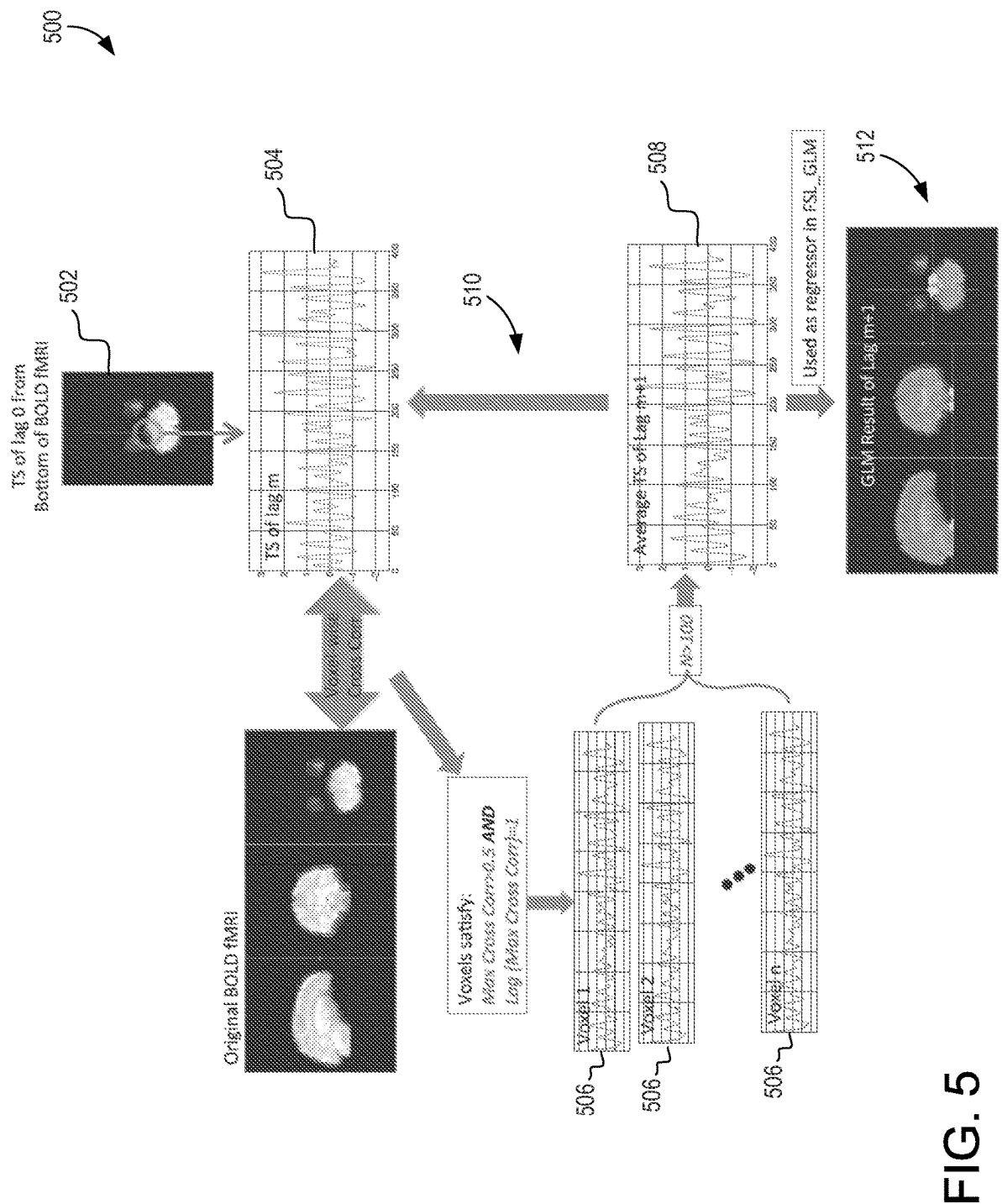
FIG. 5 is a flow diagram depicting an example of a recursive procedure to extract progressive regressors, in accordance with the present disclosure.

The steps associated with process blocks 306 though 312 are visually illustrated in the example process 500 shown in FIG. 5. Specifically, using BOLD fMRI image data 502, a time series 504 corresponding to a current regressor (for example, of lag time m=0) is utilized in a voxel-wise cross correlation analysis to identify a number of time series 506 corresponding to voxels that satisfy the pre-defined selection criterion, as described. If an iteration exit condition is satisfied, for example, the number of time series 506 exceeding 100, an averaged time series 508 is then computed using time series 506, to determine the next regressor (for example, of lag time m+1). As indicated generally by 510, this process may be repeated, with time series 508 being used in the place of time series 504. The generated regressors may then be used in a statistical analysis, as indicated generally at 512.

Figure 12:
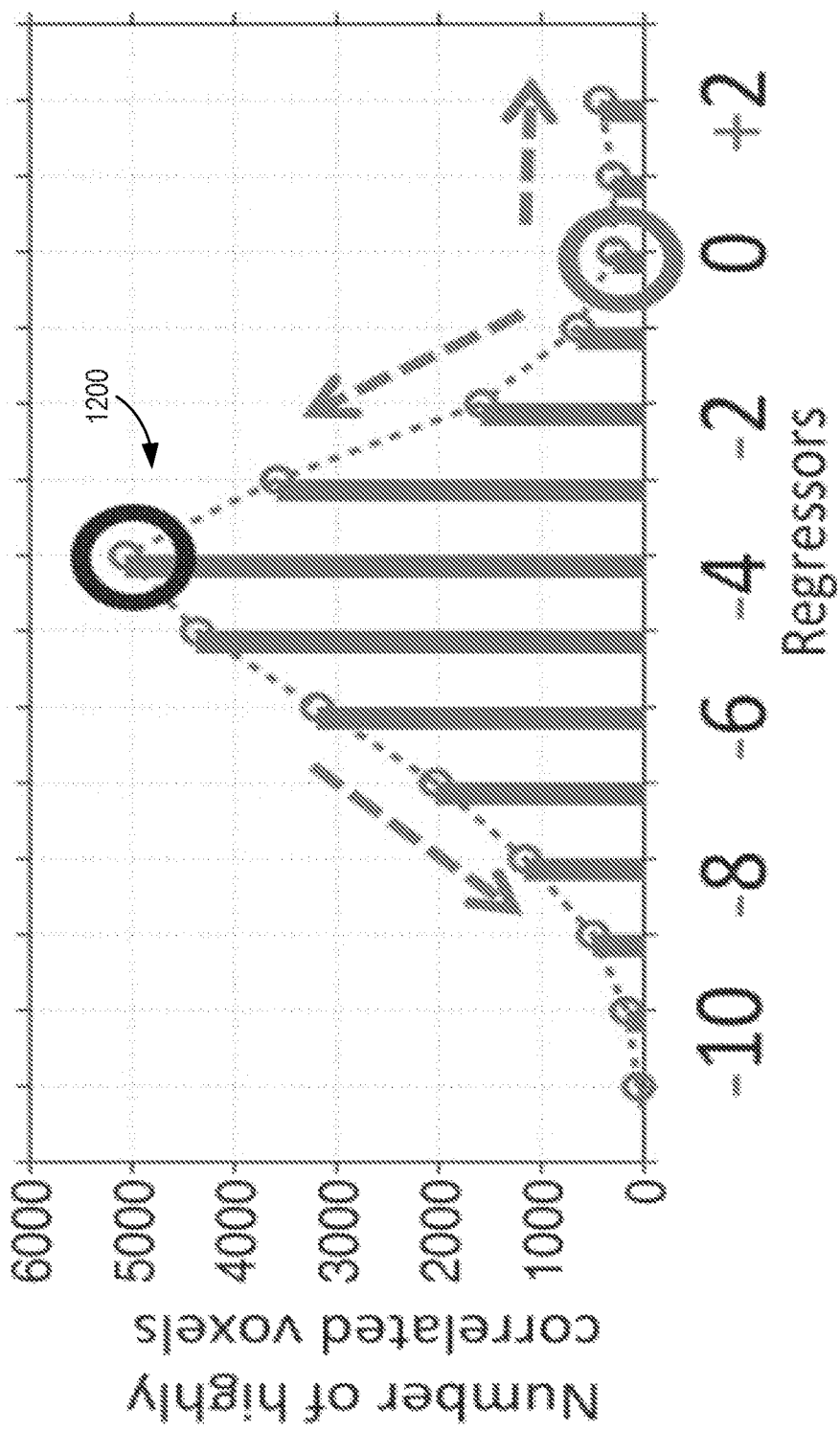
FIG. 12 is a correlation graph showing the number of highly correlated voxel for each regressor determined in accordance with the present disclosure.

The above-described recursive procedure allows for extracting evolving systemic LFO's at every iteration step. However, the temporal trace of any seed voxel may be influenced by regional fluctuations (in addition to systemic fluctuations), which might lead to inaccurate results. Therefore, in accordance with some aspects of the present disclosure, a second recursive procedure may be implemented to optimize results. Specifically, this includes identifying from regressors generated in a first recursive procedure, as described above, the regressor with the most correlated voxels. Then, the time series of the identified regressor is then set as the optimized seed regressor, and used to perform a second recursive procedure, in a manner similar to steps 308-310 of process 300 above. By way of example, FIG. 12 shows an example correlation graph that depicts the number of highly correlated voxels for regressors determined. As indicated by 1200, regressor with time lag −4 from the seed regressor has the largest number of highly correlated voxels. Therefore, the time series of regressor −4 may be used as an optimized seed regressor at process block 306.

As described, in accordance with aspects of the present disclosure, dynamic z-statistic maps may be generated to illustrate dynamic changes in activation patterns representing cerebral blood flow. Specifically, generated regressors may be utilized in a general linear model (GLM) analysis of the fMRI BOLD data. Autocorrelation correction need not be used, since the correlation in voxel-wise BOLD signal time courses between one time point and another is advantageous for identification of new voxels at each temporal shift. The resulting z-statistic maps from each regressor may then be concatenated over time according to the sequence of the regressors being used, such as for example from the largest positive number to the largest negative number.

To achieve a Bonferroni correction for the concatenation of the z-statistics maps, a scaled p-value may be used in proportion to the number of maps. As a result, the z-threshold may be larger than a certain threshold value, such as, for example 3.5, to facilitate a display. In one aspect, the z-threshold may be 4, meaning that the max z-value (out of concatenated z-statistic maps) is to be bigger than 4 for a voxel to be considered significant. In addition, to be more accurate regarding the temporal evolution of the pattern, the z-maps may be normalized by scaling the maximum value (of the concatenated z-statistics maps) at each significant voxel to be 1. As such, the normalized result can then be viewed to assess, for example, the dynamic flow of the LFO through the brain.

In another aspect of the present disclosure, correlation maps may be calculated using fMRI data from multiple subjects. Each correlation map may be obtained by calculating a voxel-wise correlation coefficient (CC) (instead of using GLM) with each regressor. The maps may then be concatenated over time, as described above. In this case, the changes in CC of any voxel may then be monitored as the regressor evolves. While this approach may not be as statistically rigorous as the previous GLM analysis, it offers direct and meaningful insights from the aspects of signal processing, and is therefore useful. In one aspect, for each subject, the numbers of voxels with correlation value exceeding a threshold, such as for example, 0.3, may be plotted against the time shift used in the corresponding regressors. This graph can be used to assess the brain areas (number of voxels) progressively affected by a perfusion, while the slope might indicate speed of the perfusion process.

In yet another aspect, delay maps may be generated from the concatenated maps (4D) to show dynamic information in one 3D image. A color may assigned to each voxel that indicates which time shift corresponds to the maximum z-value for that voxel. By observing the range of color changes in the map, a dynamic evolution, such as for example, of the LFO in the brain, may be assessed.

The above-described methods may be further understood by way of an example. The example is offered for illustrative purposes only, and are not intended to limit the scope of the present disclosure in any way. Indeed, various modifications of the disclosure in addition to those shown and described herein will become apparent to those skilled in the art from the foregoing description and the following examples and fall within the scope of the appended claims. For example, specific examples are with respect to dynamic mapping of brain blood circulation during resting states using BOLD fMRI data, although it will be appreciated that analysis of non-resting states, or neuronal activation, such as during administration of a stimulus, or drug, may also be considered within the scope of the present disclosure. Likewise, process parameters are recited (for example, imaging parameters, signal processing parameters, and the like) that may be altered or varied based on variables such as time, frequency, repetition and so forth.

Example

In this study, a new MRI data-driven method was applied to resting state BOLD fMRI data to dynamically map brain blood circulation. The regressors used at each time point to track blood flow were derived from the BOLD signals themselves using recursive procedures, as described. Since this analytical method is based on fMRI data alone (either task or resting state), it does not require a special scan sequence (i.e. ASL) or an external recording device (i.e. NIRS). It can be performed independent from the actual functional analyses, and may therefore not interfere with fMRI results. In addition, it offers extra information in cerebral blood flow simultaneously recorded with the functional study. Lastly, the sensitivity of the new method may be enhanced by very short TR BOLD image acquisitions (e.g. TR=0.4 s) that allow full sampling of the heart rate for subsequent filtering of other known physiological processes including HR and respiration.

Protocols and Instrumentation fMRI resting state studies were conducted in 7 healthy participants (3M, 4F, average age±standard deviation (SD), 27.1±8.5 years). In the resting state studies, participants were asked to lie quietly in the scanner and view a gray screen with a fixation point in the center. The resting state scans lasted 360 s for 3 participants and 600 s for 4 participants for testing purposes. All MR data was acquired on a Siemens TIM Trio 3T scanner (Siemens Medical Systems, Malvern, Pa.) using a 32-channel phased array head matrix coil. After acquiring a high resolution localizer image, (MPRAGE, TR/TI/TE=2530/1100/3.31, 256×256×128 voxels over a 256×256×170 mm sagittal slab, GRAPPA factor of 2), multiband EPI (University of Minnesota sequence cmrr_mbep2d_bold R008) data was obtained with the following parameters: (450 (task), 900 or 1500 (resting state) time points, TR/TE=400/30 ms, flip angle 43 degrees, matrix=64×64 on a 220×220 mm FOV, multiband factor=6, 30 3.0 mm slices with 0.5 mm gap parallel to the AC-PC (anterior commissure-posterior commissure) line extending down from the top of the brain.

Evolving Regressors

Figure 6:
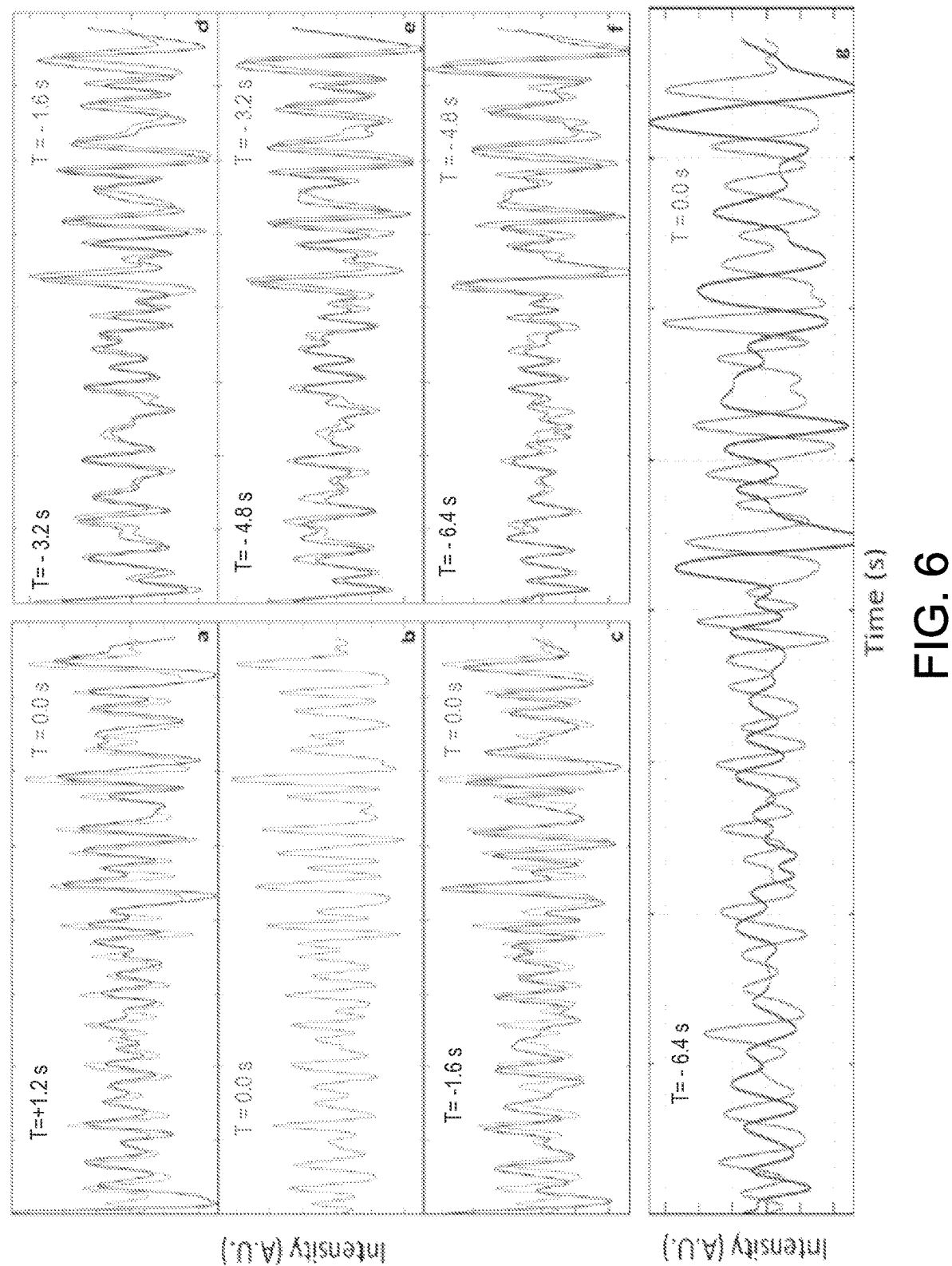
FIG. 6 is a graphical depiction illustrating examples of regressors generated by the recursive procedures over several time shifts relative to a seed voxel, in accordance with the present disclosure.

FIG. 6 illustrates regressors generated for one participant using a recursive approach as described herein. The regressors are described by time shifts between +1.2 sec and −6.4 sec in relation to a seed voxel. The temporal traces of the BOLD signal from the zero shift seed (b) were evolved both forward and backward in time. The time span of the regressors with significant brain correlations was about 7.6 sec (1.2 sec+6.4 sec=7.6 sec), which is within the range of the cerebral circulation time of healthy participants. The time course of the seed (no time shift) was plotted in (b), and the regressor with +1.2 sec time shift (together with the seed's time course) was plotted (a). Also, regressors (c) through (f) were plotted together with a time shifted regressor (shifted in time by −1.6 sec), for comparison.

Figure 7:
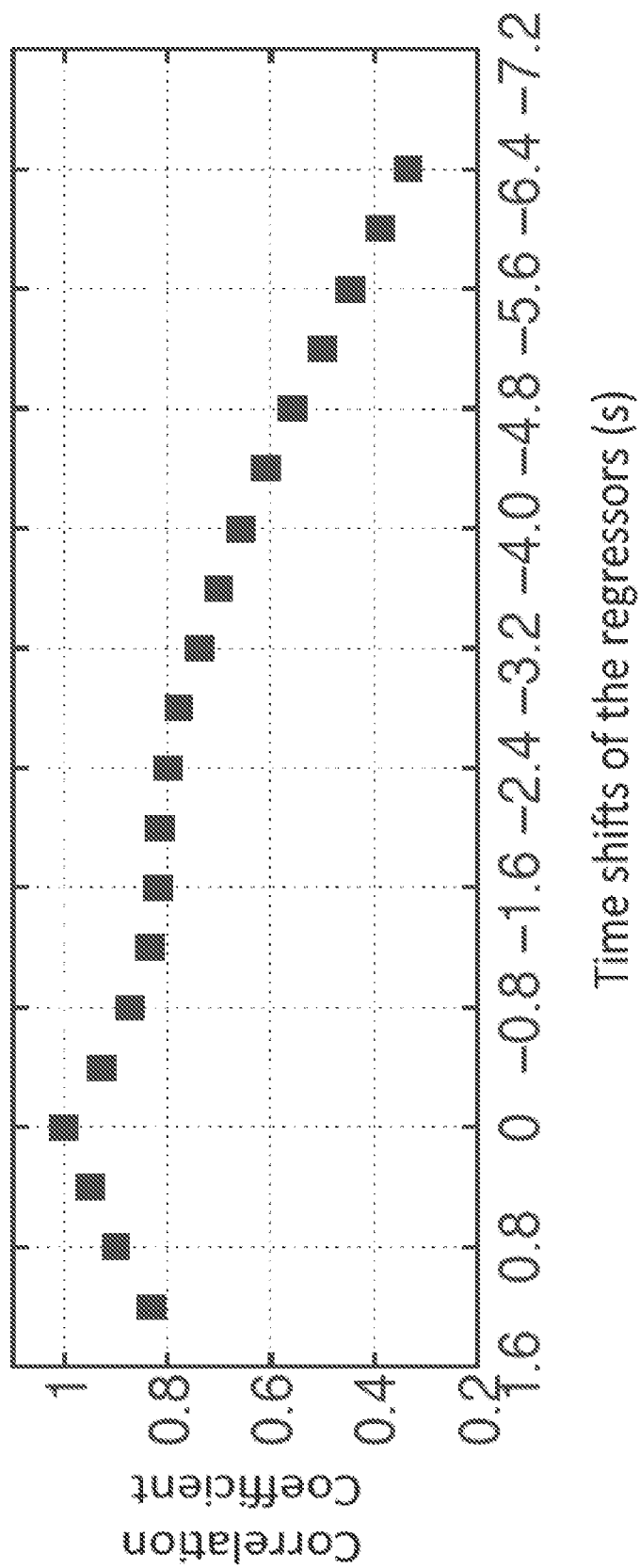
FIG. 7 is a graphical depiction illustrating an example of correlation coefficients as a function of time shifted regressors, in accordance with the present disclosure.

In addition, the correlation coefficient was also calculated between the seed regressor (i.e. the regressor with zero shift) and the rest of the regressors, which had been lined up with the seed regressor temporarily by its shifts are shown in FIG. 7, illustrating a clear decline of the correlation coefficients with regressor evolution.

The graphs of FIG. 6 demonstrate that a great similarity (R~0.85) exists between regressors with little time difference (1.6 sec in most cases). Since the smallest time shift (i.e. resolution of time lags) in this study was 400 msec, those regressors with 400 msec time shift were observed to be even more similar (data not shown). In addition, the small variations between the regressors appear from the magnitude of fluctuations and time shift. However, the regressors are not static, since variations can be accumulated as the number of recursive steps increases. This shown in FIG. 6 (g), the regressors of time shift 0 and −6.4 sec illustrate a clear dissimilarity (R~0.37). The visual difference in these two regressors is representative of the accumulative effect from the regressors' evolution over many iterations occurring over a relatively long time period (6.4 sec).

As shown, the systemic LFOs in BOLD fMRI are not static. The blood-related signal detected at any voxel is the integrated signal from all the paths of the blood flow that lead towards that point (i.e. summation of many signals with different delay times and amplitudes). Therefore the LFO signal may vary according to its location in the cerebral vasculature. Previously, a near infrared spectroscopy (NIRS) method was able to detect fundamental low frequencies in the BOLD signal. However, a strongly diminished sensitivity to detecting NIRS correlated cerebral voxels was present in that approach due to the fact that dynamic LFO changes in brain are invisible to NIRS measures collected in the periphery.

By contrast, in the approach presented herein, the regressors are progressively 'pulled out' from the BOLD data at the temporal resolution (time shift) decided by the TR. Once a vascular seed is chosen, at every subsequent step, the regressor for the next time shift (1 or −1) is derived by averaging the time courses of all the voxels that have the highest correlation coefficient with the current iteration regressor. Therefore the next regressor will likely be very similar to the current one, with only minor variations reflecting signal changes due to blood movement, as demonstrated in FIG. 6 (a) through (f). This confirms that the blood-related BOLD signal does change as the blood flow through the complicated cerebral vasculature.

A benefit of using the bottom slice of an fMRI scan is that it includes large blood vessels (including both arteries and veins), and a relatively small amount of neuronal tissues, which make it easy to select a vascular seed voxels. A seed selected from a bottom slice may represent either the beginning of the cerebral blood flow (if located on an artery) or the end of it (if located on a vein). In this way, the regressor search procedure may be simplified by defining the direction of the search. For example, if a venous seed is used, the corresponding time course would represent the blood signal at the end of its passage throughout the brain. Thus only blood signals previous to the seed may need to be searched (i.e. positive time lag). If the seed was positioned over other easily identifiable large vessels (e.g. superior sagittal sinus), then the search for the next regressor may go both ways in time (meaning + and − in the time lags). Most importantly, the choice of seed voxels might not affect the results, since if the wrong seed were selected (with low SNR in the blood LFO), the recursive procedure would die out after a few iteration steps.

Among all participants of this study, seeds successfully selected originated in veins (judging from the direction in which correlations with the brain were found). There are several possible explanations for this. First, previous work showed that although LFO are present in all blood vessels, their strengths in the BOLD signals vary according to the vessel type. For example, in arteries, the power of blood-related LFO in BOLD signal time courses is relatively small given that the dominant signal stems from the cardiac pulsation. Mixed with other physiological noises, the LFO in the arteries are hard to detect even after the band pass filtering. By contrast, the blood signals in veins integrate signals of different phases due to the different paths taken. This tends to reduce the power of the higher frequency signals (e.g. cardiac pulsation signal) due to phase cancellation, thus strengthening the power of low frequency signals which results in dominant LFO in the BOLD at veins. Second, even if an arterial seeds were initially selected, since its LFO signals are weak compared to noise, the recursive procedure might terminate early.

Dynamic Maps

Figure 8:
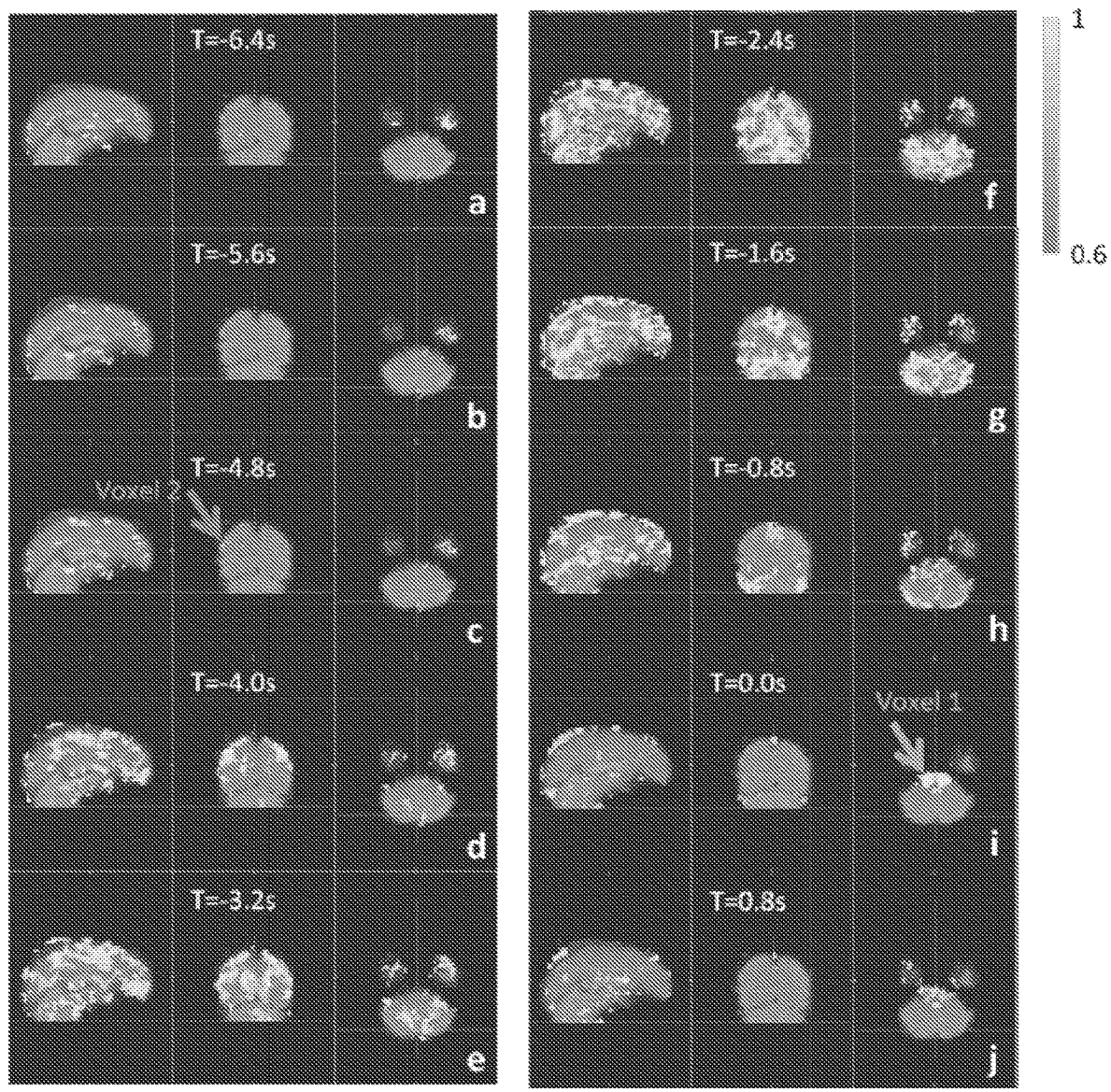
FIG. 8 is a graphical depiction illustrating examples of normalized z-maps, in accordance with the present disclosure.
Figure 8:
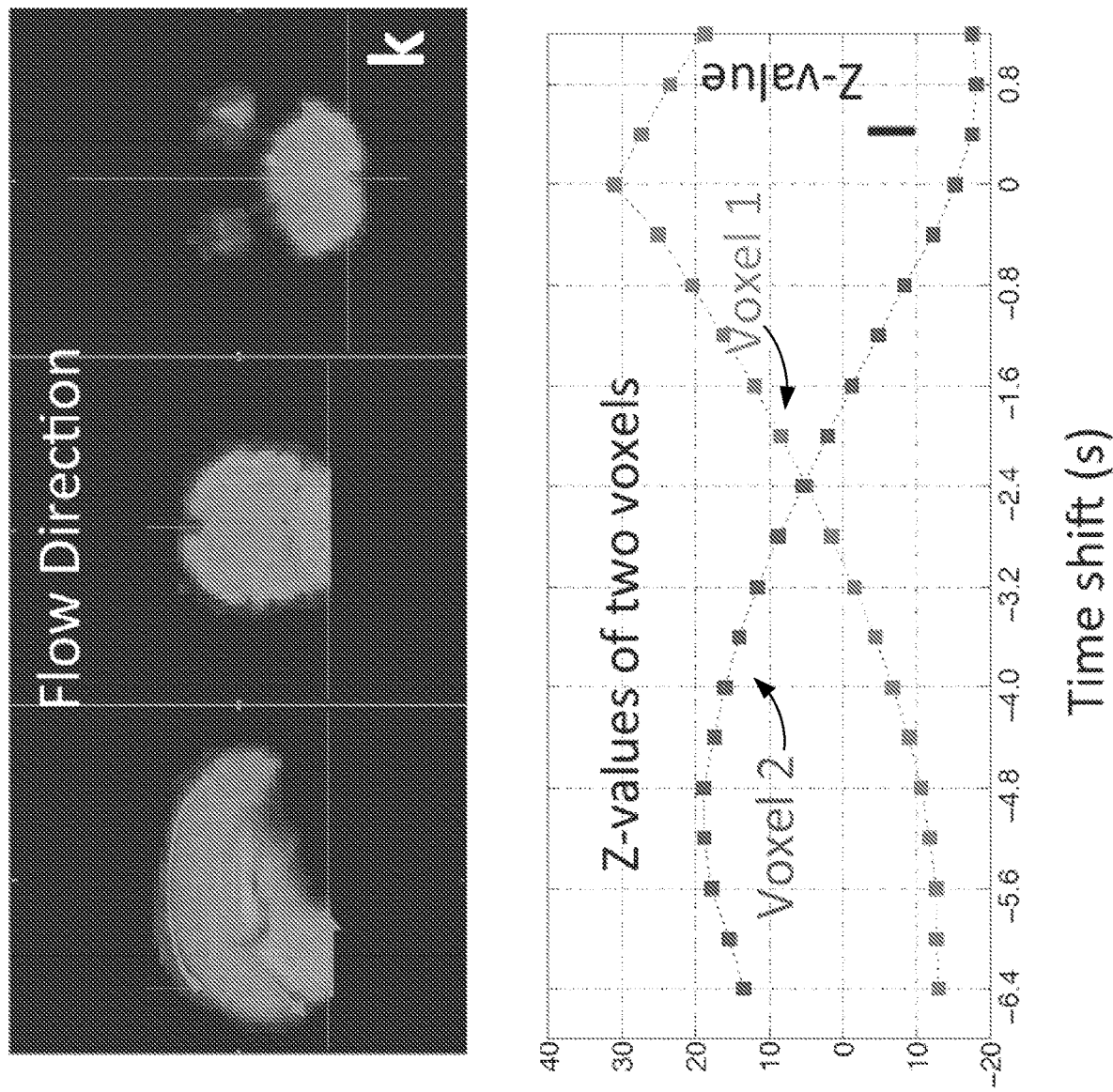

FIG. 8 (a) through (j) show normalized z-maps as the result of a GLM analysis, as described above, according to the temporal shift in the corresponding regressor. The dynamic changes in the activation patterns represent cerebral blood flow. For example, in a sagittal view, the initial activation patterns were observed in areas densely populated with or supported by large arteries, such as polar frontal arteries, medial frontal arteries, and so on. The activation patterns gradually move towards the areas of drainage systems, such as the superior sagittal sinus or straight sinus. In the coronal view, the patterns shift from posterior cerebral arteries near superior aspects of the brain to the middle and then end in the superior sagittal sinus at top and transverse sinuses at the base of the brain. Lastly, in the axial view, the pattern of activations start at the center of the cerebellum and move in two directions (anterior and posterior), ending in the transverse sinus (or Tentorial veins) and Clival venous plexus (or Jugular bulb). Arrows in FIG. 8 (k) indicate the directions of the apparent blood flow in the orthogonal graphs, as seen in figures (a) through (j).

To demonstrate the utility of the normalization procedure, the z-values of two example voxels from the concatenated results before normalization are shown in FIG. 8 (l). The traces reflect typical changes in the z-values as result of the temporal shifts in the regressors. The arrival time of the LFO wave, namely the peak position of the trace in FIG. 8 (l), and the duration of its passage through the voxel, or width of the trace in FIG. 8 (l), may be more important than the z-values themselves in assessing the dynamic evolution of each voxel. In fact, the large range of the z values, likely due to the various blood content in the voxels, makes it difficult to display the results and decreases the sensitivity of the dynamic map since voxels with high z-values stay activated much longer. Therefore, normalizing the z-values from each significant voxel may be advantageous, for example, max $z>4$.

The dynamical blood flow patterns may be further seen by combining the concatenated normalized z-maps in a movie (not shown). For the images shown in FIG. 8, the passage of the LFO was clearly detected, with the movie played at a rate of 0.15 s/frame rate (a factor of 2.67 speedup), although other values are possible. Moreover, it was observed in axial images that the patterns started from middle areas (heavily supported by the middle cerebral arteries) to the drainage veins located at anterior and posterior of the brain (superior sagittal sinus) and the walls of the lateral ventricles.

It was observed that the activated voxels in each of the normalized z-maps of FIG. 8 were distributed throughout the brain. This is noteworthy because the temporal traces of remote voxels that are located as far away as prefrontal cortex and posterior cerebellum can be highly correlated with the same regressor. This indicates that the LFO component of the BOLD signals from these voxels evolved roughly the same way. The LFO were 'piped' into the brain though big arteries (e.g. internal carotid artery) with no phase shift. Then, they went into different paths (arterioles, capillaries etc) as branches of the cerebral vasculature diverge. It is expected that each signal would evolve independently as it travels along its own path. The observation that some of them have evolved in a similar way, and at a the similar pace, indicates the uniformity in the fundamental structures of the cerebral blood system, reflecting likely the self-invariant properties of fractal structures found throughout biological systems.

Since the regressors were generated by averaging time courses of many voxels in the whole brain, the regional fluctuations, caused by moderate neuronal activations (e.g. resting state processes), are averaged out if their powers in the BOLD signal are relatively small compared to that of the systemic blood LFO. Therefore, the approach of the present disclosure may be largely insensitive to small neuronally driven local variations in brain blood flow, as long as these regional fluctuations are relatively small in the BOLD signal (compared to the systemic blood signal).

Perfusion Curves

Figure 9:
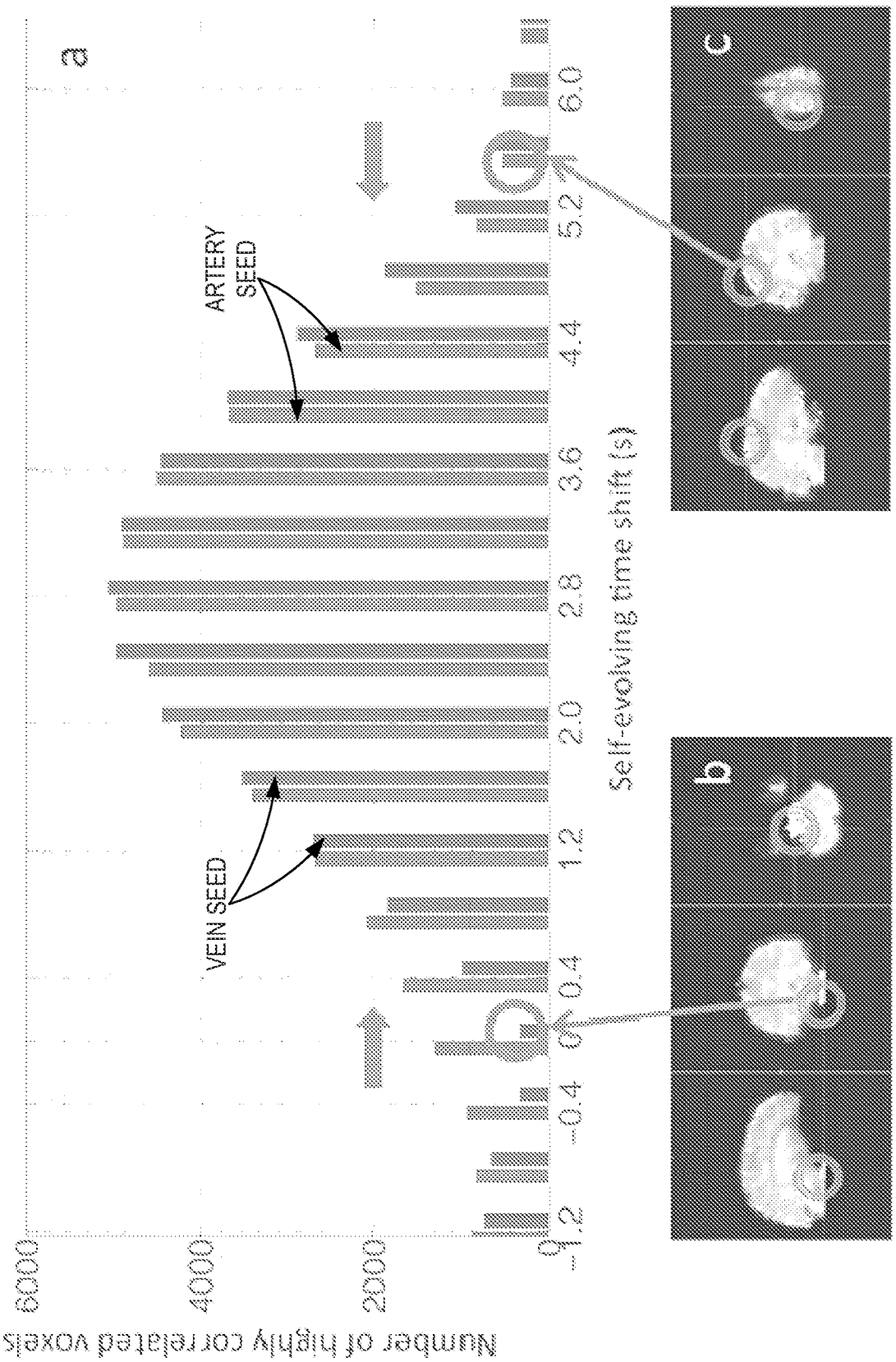
FIG. 9 is a graphical depiction illustrating examples of numbers of voxels correlated with regressors at different time shifts for a subject, in accordance with the present disclosure.

FIG. 9 (a) shows data from one study participant in a graph illustrating the numbers of highly correlated voxels versus the self-evolved regressors at different time shifts. Physiologically, this graph shows the dynamical nature of areas being perfused by the cerebral flood flow. In this example, approaches as described above, were conducted on the same BOLD fMRI data using different initial seed voxel, namely seeds located both in arteries and veins. For the seed location selected in veins the number of voxels highly correlated with this seed are identified with the left circle of FIG. 9 (b). Similarly, the number of voxels highly correlated obtained from an arterial seed is identified with the right circle, shown in FIG. 9 (c). The left arrow indicates the main evolving direction in time ('+') for the seed located in the veins, while the right arrow points toward the main evolving direction in time ('−') for the arteries. The same number of steps was generated in each automatic procedure, resulting in a total circulation time of 7.6 sec. As observed, similar numbers of highly correlated voxels were produced at each step regardless of whether the search occurred in the arterial or the venous direction in time, leading to a Gaussian shaped curve. This indicates that the vascular structure is mostly symmetrical, and that the time of perfusion is symmetrical, meaning that it takes a similar amount of time for the blood to flow in to the tissues as it takes for the blood to flow out.

Figure 10:
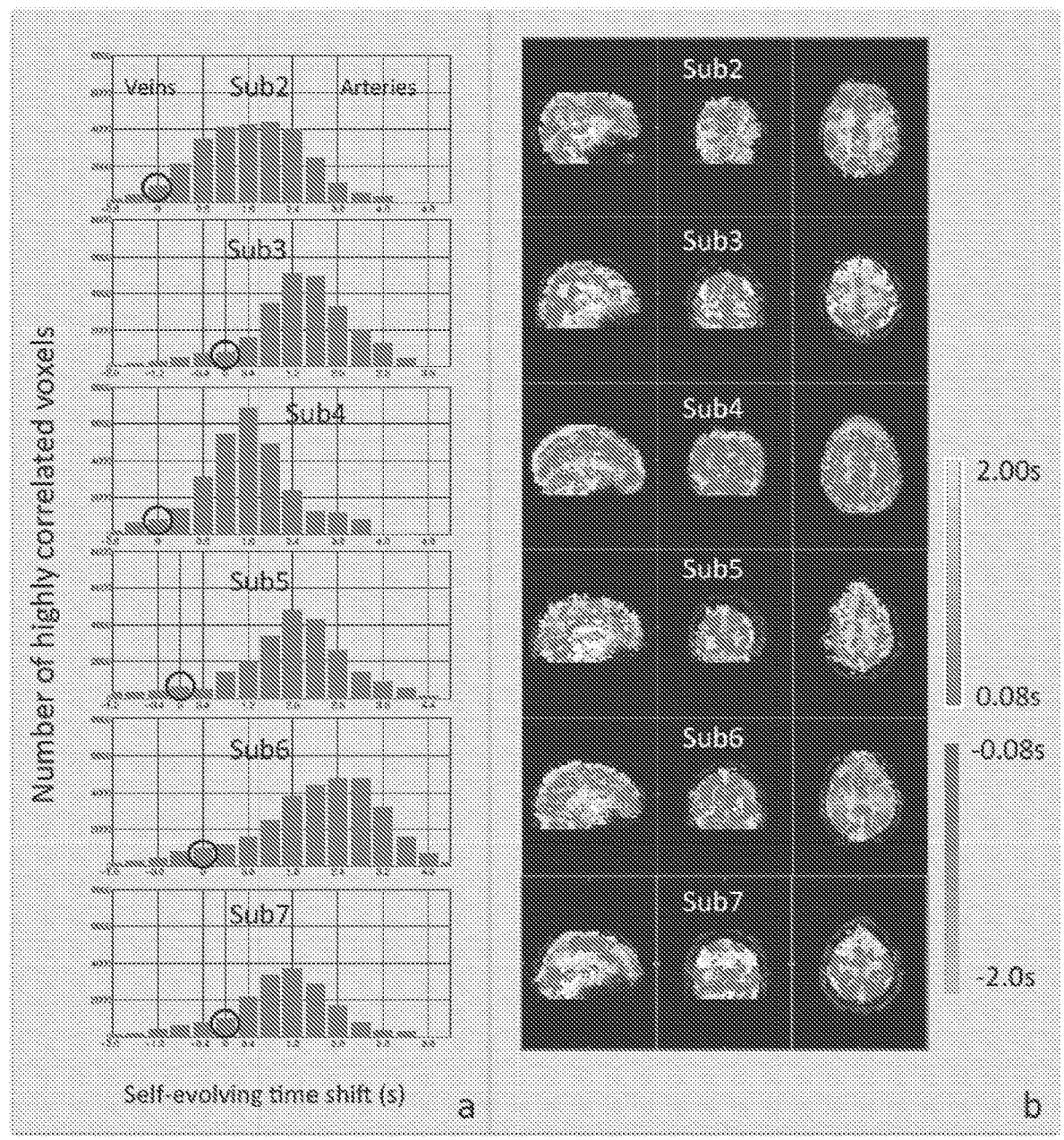
FIG. 10 is a graphical depiction illustrating a comparison of numbers of voxels correlated with regressors at different time shifts and corresponding delay maps for several subjects, in accordance with the present disclosure.

FIG. 10 (a) shows similar graphs for several other participants. Of note is that the shapes of the perfusion curves are subject-specific, resembling Gaussian or skewed Gaussian curves. In FIG. 10 (a) the circle indicate the zero-delayed seed voxels that generated the first regressor, and the number of voxels correlated with seed0. In this examples, the circulation times are between 4.4 sec and 6 sec. Here, it seems that inflow process (from arteries) is faster than the drainage process (the curve was skewed towards arteries). Given that these data are from healthy participants, it may be hypothesized that dramatic deviations in the shape of these frequency histograms might indicate some abnormality in the blood circulation, although, additional studies may elucidate the meaning of these distributions further. Moreover, the current method may be more sensitive to veins than the arteries which might affect the shape of the curves to some extent.

Time-Delay Maps

In addition to the graphs of highly correlated voxels, orthogonal time delay maps were also generated, representing different time delays, as shown in FIG. 10 (b). In brief, cerebral blood flows in sequence, as colored by light blue, blue, red and yellow. As a result, drainage systems are mostly colored with red and yellow, indicating they are located towards the end of the blood passage. In contrast, the areas with light blue are mostly in the top middle section of the brain supplied mostly by the middle cerebral arteries. The color pattern differences between participants reflected individual differences in cerebral blood flow, which may be due in part to heterogeneity between the seed voxel location for each of the participants.

Robustness of the Method

FIG. 9 (a) shows the perfusion curves as result of analyzing a single data set with two separate analysis procedures that differed only in the choice the first seed, demonstrating the robustness of the current method in two ways. First, the two lines were heavily overlapping, with almost identical corresponding movies generated, thus indicating that the analysis procedure is quite stable, regardless of the choice of the seed and direction of the search. Second, the number of voxels from the red seed has the largest deviation from the blue line. This may show that the seed choice may not have been ideal, yet, after a few evolving steps, the procedure might be able to correct itself. This feature is advantageous, demonstrating that the blood-related BOLD signal is fairly dominant and consistent in corresponding voxels. Thus its common value can be extracted in a few steps, a value that is relatively insensitive to the initial conditions. As mentioned previously, if the seed has none or little blood-related LFO, the recursive procedure will either not start or it will stop in few steps. This also demonstrates the robustness of the method.

Impact of Short TR

Use of a short TR for the fMRI scans was advantageous in this study, since the TR dictates the time resolution of the dynamic map by its relationship with the regressor evolution condition. Typically, cerebral circulation time of cerebral blood flow is roughly 4 to 7 sec. If the TR were chose to be around 2 to 3 sec, then only about 2-4 dynamic maps may be generated, which dramatically reduces the resolution in dynamic maps. However, due to the low frequency (less than 0.2 Hz) of the blood signal of interest, the BOLD signals with longer TR (2-3 sec) may have enough information. Therefore, one can oversample the BOLD signal of long TRs (e.g. 2 sec) with much smaller TRs (e.g. 400 ms) in order to increase the time resolution of the dynamic map.

Figure 11:
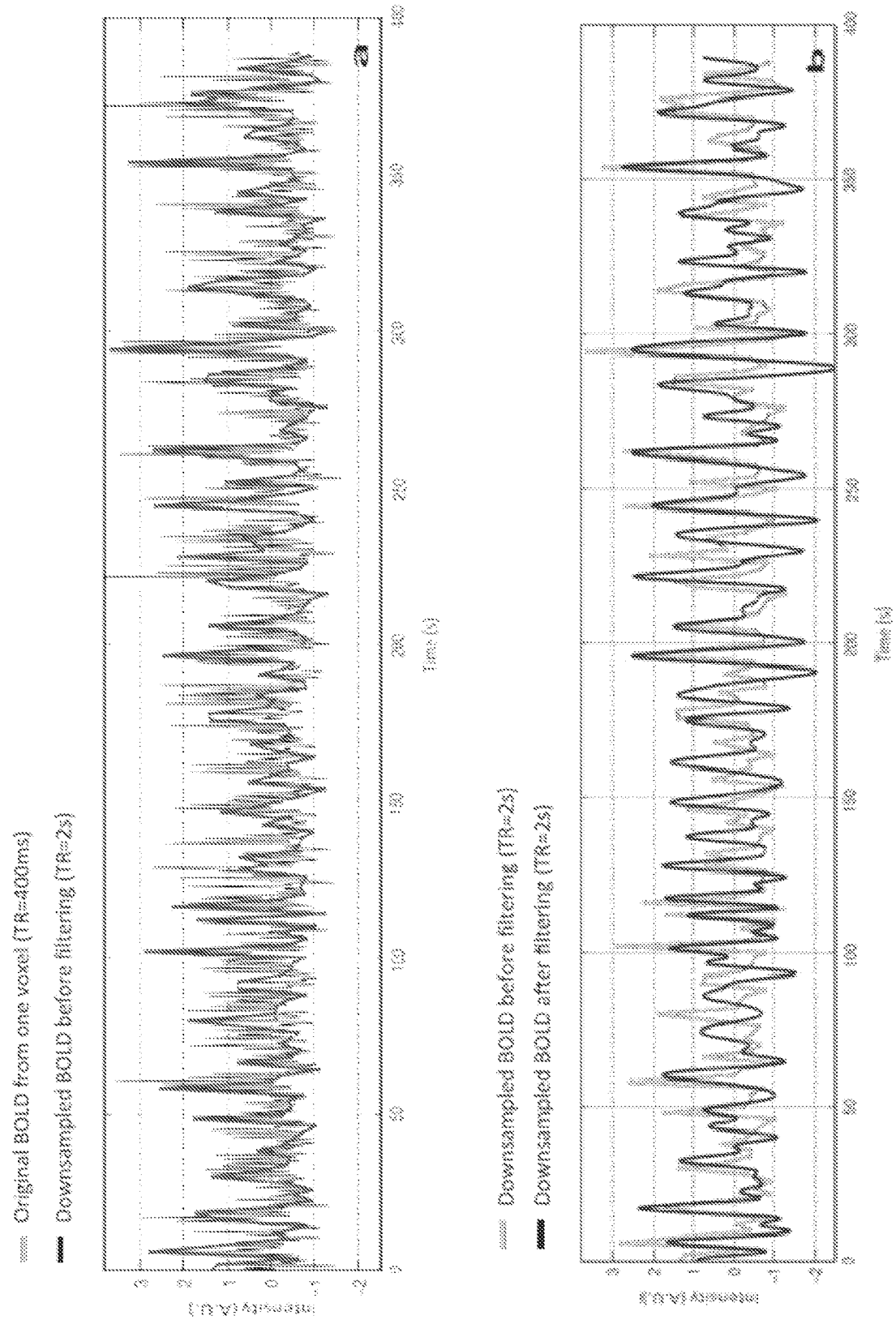
FIG. 11 is a graphical depiction illustrating the impact of repetition time used in an fMRI scan, in accordance with the present disclosure.

In this approach, however, other physiological fluctuations in the BOLD signal present, such as cardiac pulsation wave traveling along the blood vessels, are also aliased into the BOLD with long TR. This effect can be seen in FIG. 11, where the unfiltered time trace data from FIG. 2 was downsampled to every 2 sec to simulate the BOLD signal recorded at a 2 sec TR. The resulting temporal trace, simulating a higher TR appears very different in FIG. 11 when compared to temporal trace with lower TR, which is mostly due to the aliased cardiac signal.

The data was then oversampled to a TR=400 ms and the recursive procedure was run to generate the dynamic map. The result still provided an ability to track some of the blood flow as seen before, however, with a time of the flow that was much shorter (automatically generated time span is 3.2 sec) than previously obtained from the same data set. The deviation might be explained by the influence of the cardiac pulsation aliased in the BOLD fMRI, as the cardiac wave also travels along the blood vessels as the LFO, however with different speed and possibly different passages. The method may end up tracking two traveling signals (i.e. LFO and cardiac), instead of one, resulting in different dynamic maps with different speeds. The short TR offers an easy and very effective solution, by filtering out other physiological noises. Since these noise signals are fully sampled by the short TR, it is relatively easy to remove them using a bandpass filter. Therefore, this approach could be applicable to the data with longer TRs, when there is little or no aliased physiological noise in it. However, a short TR sequence may advantageously offer more accurate results after fully removing the confounding noise.

Denoising

FIG. 10 shows the number of correlated voxels versus the time shifted with corresponding delay maps for several participants of this study. It is seen that most voxels are highly correlated with the blood LFOs at certain time shift, demonstrating that the majority of the voxels are affected by systemic LFO, especially in resting state studies when the neuronal signals are relatively small. Previously, it has been proposed to identify and remove LFO using NIRS signals and their temporal shifts, recorded simultaneously at forehead or the periphery. However, as demonstrated in this study, the LFO evolve, and thus using static NIRS regressors might improve some BOLD signals, but not all. Moreover, it has also been demonstrated that some resting state networks were affected by systemic LFO in a certain sequence matching the blood perfusion, indicating that these networks' signals could be greatly influenced by the various temporal shifts of the LFO. Therefore, the approach of the present disclosure can be used to identify the non-neuronal LFO effectively and can dramatically improve the SNR for the BOLD and accuracy of the RSN.

Quantification of the Parameters

In the flowchart illustrated in FIG. 5 several empirical values were used, due to the yet unclear origin and function of the LFO signal. LFO signals typically do not have a well-defined spectral range, occurring generally in a spectral band similar with other signals, such as those stemming neuronal activations, making it hard to isolate systemic LFO in the brain. In previous research, LFO were measured in the periphery (i.e. finger and toe) using NIRS during fMRI scanning. The results showed that LFO (i.e. Δ[tHb]) measured at finger (or toe) were highly correlated with many BOLD signals in the brain with a time shift, confirming that the LFO are systemic. The spectral features of these LFO were investigated by only correlating signals between the finger and the toe, without neuronal signals, yielding correlations in the spectral range 0.05~0.2 Hz. A similar range chosen for this study appeared sufficient and effective in producing the dynamic maps.

In addition to spectral range, a threshold number for highly correlated voxels was set to be 100 in the condition for terminating the recursive procedure. This threshold was based on a 1-5% of the maximum number of voxels in the whole procedure (e.g. in FIG. 9 the maximum number is about 5,000 at step 11, and so the threshold may be set to be 2% of this value). If the procedure is not terminated properly, the recursive procedure may continue. The number of voxels being selected is likely to increase again. This is probably due to the pseudo-periodic feature of the LFO signals. For example, the periodic signal of LFO (0.05~0.2 Hz) is oscillating every 5~20 sec. As such, other ways to terminate the procedure in addition to just using the number of voxels are possible. For instance, the number of highly correlated voxels by each evolved regressor may be monitored, such as shown in FIG. 9 and FIG. 10. If the number starts to increase again after reaching the minimum, the process may be stopped. Moreover, a systematic way may be developed to decide if the seed is the 'correct' one or the 'wrong' one.

Sensitivity of Different Vessels

As shown in FIG. 8, the dynamic patterns are mostly seen in gray matter and drainage veins. The network of arteries, which is at the base of the brain, is not as clear. As was discussed previously, the LFO signals are dominant signals in the voxels in the gray matter and veins, while cardiac signals are dominant in the arteries. Therefore, the areas of gray matter and veins are much easier to map using the LFO signals, which was demonstrated separately by showing that the arteries were clearly mapped out when the cardiac signal was used as the regressor. As result, the sensitivity of the method may be biased towards the gray matter and veins.

Optimized Procedure

Figure 13:
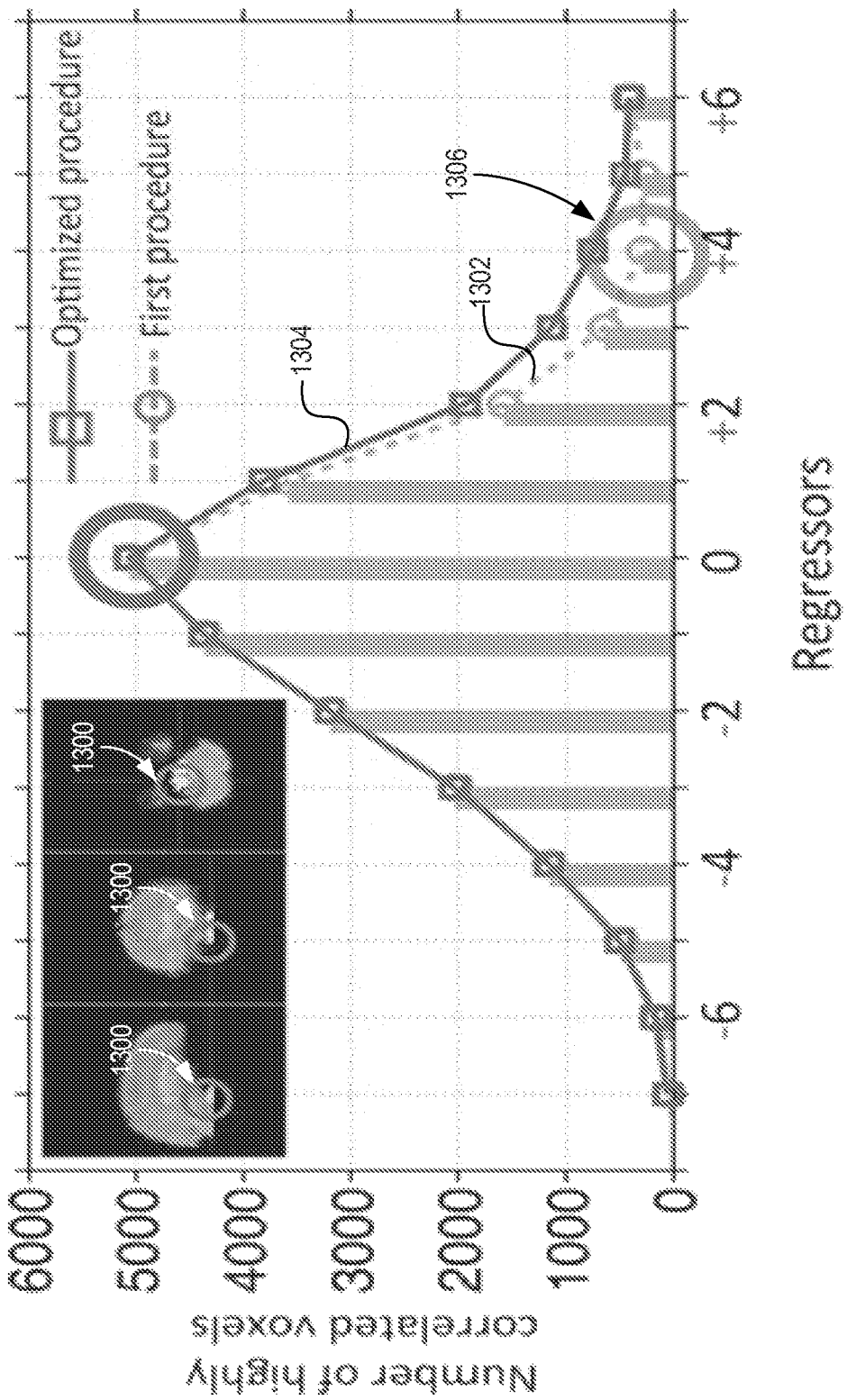
FIG. 13 is another correlation graph comparing a first recursive procedure versus an optimized recursive procedure, in accordance with aspects of the present disclosure.

FIG. 13 shows the process and results using an optimized procedure performed on one study participant. The inset of FIG. 13 shows the location 1300 of the seed from the last slice of the fMRI scan. The correlation graph from the first procedure 1302 along with the correlation graph of the optimized procedure 1304 are shown in FIG. 3. Deviations between the results between the first and second, or optimized, procedure are appreciable, with the largest differences occurring at the seed regressor of a single voxel 1306.

As described, most regressors were generated by averaging the temporal traces of the voxels selected by the previous regressor. The averaging process emphasizes the commonalities of the signals in these selected voxels (i.e., systemic LFOs of same time shift) while eliminating the other signals in the voxel, including regional neuronal/blood signals, other physiological noise, and so forth. However, if the seed is from a single voxel, it does not benefit from averaging and thus is contaminated by the regional fluctuations/noise. This contamination explains the large deviation at the seed regressor observed in FIG. 13; it also influences the accuracy of the next few regressors. A region of interests (ROI) analysis, which defines a cluster of voxels based on structure/functional similarities to boost the signal to noise ratio (SNR), may not suitable because; (1) blood vessels are generally small compared to the size of the voxel; (2) each blood vessel has unique shape and direction, which is not well matched to an ROI of regular shape; and (3) most important, the seed is supposed to reflect the travelling systemic LFOs at one physical point, averaging a duster of voxels whose signals may have different time shifts would cancel the signal instead of strengthening it.

The above described optimized procedure was developed to solve this problem. After a first recursive procedure, a second analysis starts with a new seed regressor, which is the result of averaging the most voxels selected by the previous procedure and thus represents the most accurate systemic LFOs shared by these voxels. The new seed can be regarded as resulting from a special "ROI." The unique feature is that this spatially distributed, but temporally compact ROI is identified by the previous procedure. Finally, it is observed that the time span of the correlation graph in FIG. 13 is about 5.2 s (i.e., 0.4 s 3 1355.2 s), which is in the range of the cerebral circulation time of healthy participants.

In summary, perfusion fMRI is widely used clinically to assess the changes in blood flow caused by pathology. Recently, it has also been applied to functional studies. However, assessing perfusion information during functional studies is difficult given the limitations of the technique, such as low temporal resolution, invasiveness (i.e. use of exogenous contrast agent), low SNR, and complexity in combination with fMRI.

Therefore, the present system and method is presented herein that utilizes a data-driven method to analyze fMRI data for use in tracking cerebral blood flow or neuronal activation dynamically using an iterative evolution of analysis regressors. Other analysis approaches using fixed regressors, generally, cannot fully characterize the evolving and progressive nature of signals in the brain representative of circulation or neuronal activation. By contrast, the system and method presented herein provide a data-driven approach, whereby self-evolving regressors are generated using an iterative evolution, allowing the data itself to generate in an unbiased manner the necessary analysis regressors. Specifically, an estimate of the response shape at a different time (i.e. new regressor) can be generated by, for example, averaging all voxels that have high correlation with a temporally shifted version of the regressor (cross correlation) at a given time shift. This process recursively repeated, may be used to generate, for example, dynamic activation maps.

The system and method of the present disclosure utilize intrinsic systemic oscillations (such as low frequency oscillations) in the BOLD fMRI signals as a tracer to track, for example, cerebral blood flow, dynamically. In the method, an initial time course is extracted from an fMRI voxel with a desired characteristic. For example, a voxel representative of blood vessels in the bottom slice of an fMRI scan, which reflects global hemodynamic variations. Alternatively, a voxel could be extracted from an activated brain region to determined a temporal response specific to a neuronal activation. In general, as blood moves thorough the brain, or a task activation progresses, the temporal response shape may change. As such, the methods of the present disclosure allow the analysis regressor to evolve over time in a manner that reflects this change; thus, allowing for a more sensitive analysis of the dynamic process.

Demonstrations have been provided that systemic oscillations exist widely in fMRI BOLD signals, whose the temporal traces evolve as the blood propagates though the brain, and that these temporal traces can be effectively extracted using a recursive procedure and used to derive the cerebral circulation map. Moreover, the methods presented herein have been shown to be independent from functional analyses; thus, offering simultaneous and independent assessment of the cerebral blood information on top of the functional studies. In a study described herein, the method has been tested on the resting state scans of healthy participants using multiband sequences. Accurate cerebral blood circulation maps with consistent features were derived, confirming the robustness and repeatability of the method.

One benefit of the approach utilized in the present disclosure is that it involves a data-driven and automatic procedure, without need for additional measurements. Also, cerebral flow maps can be calculated using ordinary BOLD fMRI data, obviating the need for special MRI sequences. As such, the approach of the present disclosure may be applied to virtually any resting state studies. In addition to resting state results, additional valuable information about the cerebral blood flow may be produced at no further cost. This may be useful for conditions associated with aging population, stroke, Alzheimer's disease, and so forth, which are known to affect the dynamics of cerebral vasculature. Furthermore, the method of the present disclosure may be modified to track regional blood flows caused by task activations, including auditory, visual and other types of stimulations.

The various configurations presented above are examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method for analyzing blood flow in the brain of a subject, the method comprising:
    a) acquiring a set of functional magnetic resonance imaging (fMRI) data from the subject over a time period with a magnetic resonance imaging (MRI) system that measures at least one of a blood flow, a blood volume, and a blood oxygenation of the subject;
    b) analyzing the set of fMRI data to identify a target spectral characteristic related to blood flow in at least one vessel coupled to the brain;
    c) selecting, from the set of fMRI data, a seed regressor as a zero time lag signal with the target spectral characteristic;
    d) performing a cross-correlation using the set of fMRI data and the seed regressor to identify a subset of the set of fMRI data that correlates with the seed regressor greater than a threshold and is offset from the zero time lag signal;
    e) combining the subset of the set of fMRI data to determine a time-delayed regressor;
    f) repeating steps (d) and (e) to obtain a number of time-delayed regressors, wherein for each corresponding repetition, the seed regressor is adjusted using the time-delayed regressor from step (e);
    g) analyzing the set of fMRI data using the plurality of time-delayed regressors to determine a delivery of blood from the at least one vessel across regions of the brain; and
    h) generating a report of regional blood flow changes in the brain of the subject over the time period.

2. The method of claim 1, wherein step (b) further includes performing at least one of a motion correction, a slice timing correction, a spatial smoothing, and a spectral filtering.

3. The method of claim 1, wherein the target spectral characteristic includes at least one low frequency oscillation in the zero time lag signal.

4. The method of claim 3, wherein the at least one low frequency oscillation occurs in a frequency range between 0.01 Hz and 0.2 Hz or wherein the report further comprises a mapping of a dynamic evolution of the at least one low frequency oscillation in the brain of the subject over the time period.

5. The method of claim 1, wherein step (d) further comprises determining a maximum cross-correlation between the fMRI data and the seed regressor, wherein the maximum cross correlation is greater than the threshold and a time lag of the maximum cross correlation in relation to the seed regressor occurs at a value defined by a repetition time.

6. The method of claim 1, wherein the number of time-delayed regressors at step (f) is determined by the subset of the set of fMRI data from step (d).

7. The method of claim 1, wherein step (g) further comprises using a general linear model (GLM).

8. The method of claim 1, the method further comprising performing a second recursive procedure by repeating steps (d) through (f) using an optimized seed regressor at step (c), wherein the optimized seed regressor is determined from the number of time-delayed regressors obtained in a first recursive procedure using steps (c) through (f).

9. A magnetic resonance imaging (MRI) system for analyzing blood flow in the brain of a subject, the system comprising:
    a magnet system configured to generated a polarizing magnetic field about at least a portion of the subject arranged in the MRI system;
    a plurality of gradient coils configured to apply a gradient field to the polarizing magnetic field;
    a radio frequency (RF) system configured to apply an excitation field to the subject and acquire, over a time period, functional magnetic resonance imaging (fMRI) data that measures at least one of a blood flow, a blood volume, and a blood oxygenation of the subject;
    a computer system programmed to:
        a) control operation of the plurality of gradient coils and RF system to acquire a set of fMRI data;
        b) analyze the set of fMRI data to identify a target spectral characteristic related to blood flow in at least one vessel coupled to the brain;
        c) select, from the set of fMRI data, a seed regressor associated with a zero time lag signal, and consistent with the target spectral characteristic;

d) perform a cross-correlation using the set of fMRI data and the seed regressor to identify a subset of the set of fMRI data that correlates with the seed regressor greater than a threshold and is offset from the zero time lag signal;

e) combine the subset of the set of fMRI data to determine a time-delayed regressor;

f) repeat d) and e) to obtain a number of time-delayed regressors, wherein for each corresponding repetition, the seed regressor is adjusted using the time-delayed regressor from e);

g) analyze the set of fMRI data using the plurality of time-delayed regressors to determine a delivery of blood from the at least one vessel across regions of the brain; and h) generate a report of regional blood flow changes in the brain of the subject over the time period.

10. The system of claim 9, wherein the target spectral characteristic comprises at least one low frequency oscillation in the zero time lag signal wherein the at least one low frequency oscillation occurs in a frequency range between 0.01 Hz and 0.2 Hz and wherein the computer is further programmed to generate the report to include at least a mapping of a dynamic evolution of the at least one low frequency oscillation in the brain of the subject over the time period.

11. The system of claim 9, wherein, at d), the computer is further programmed to determine a desired cross-correlation between the fMRI data and the seed regressor, wherein the desired cross correlation is greater than the threshold and a time lag of the desired cross correlation in relation to the seed regressor occurs at a value defined by a repetition time.

12. The system of claim 9, wherein the computer system is further programmed to perform a second recursive procedure by repeating steps (d) through (f) using an optimized seed regressor at step (c), wherein the optimized seed regressor is determined from the number of time-delayed regressors obtained in a first recursive procedure using steps (c) through (f).

13. The system of claim 12, wherein the optimized seed regressor is determined by identifying the time-delayed regressor having a highest number of correlated voxels.

* * * * *